(12) United States Patent
Warren et al.

(10) Patent No.: US 7,432,052 B2
(45) Date of Patent: Oct. 7, 2008

(54) METHOD AND IDENTIFICATION OF DOWNSTREAM MRNA LIGANDS TO FMRP AND THEIR ROLE IN FRAGILE X SYNDROME AND ASSOCIATED DISORDERS

(75) Inventors: Stephen T. Warren, Atlanta, GA (US); Victoria Brown-Kennerly, Decatur, GA (US); Peng Jin, Marietta, GA (US); Stephanie Ceman, Atlanta, GA (US); Robert B. Darnell, Pelham, NY (US); Jennifer C. Darnell, Pelham, NY (US); Jack D. Keene, Durham, NC (US); Scott A. Tenenbaum, Albany, NY (US)

(73) Assignees: The Rockfeller University, New York, NY (US); Duke University, Durham, NC (US); Emory University, Atlanta, GA (US)

( * ) Notice: Subject to any disclaimer, the term of this patent is extended or adjusted under 35 U.S.C. 154(b) by 111 days.

(21) Appl. No.: 10/495,728

(22) PCT Filed: Nov. 15, 2002

(86) PCT No.: PCT/US02/36861

§ 371 (c)(1),
(2), (4) Date: Feb. 16, 2005

(87) PCT Pub. No.: WO03/041659

PCT Pub. Date: May 22, 2003

(65) Prior Publication Data

US 2005/0130151 A1 Jun. 16, 2005

Related U.S. Application Data

(60) Provisional application No. 60/336,249, filed on Nov. 15, 2001.

(51) Int. Cl.
*C12Q 1/68* (2006.01)
*C12P 19/34* (2006.01)

(52) U.S. Cl. .................. 435/6; 435/91.1; 435/91.2

(58) Field of Classification Search .................. None
See application file for complete search history.

(56) References Cited

U.S. PATENT DOCUMENTS

| 5,567,604 | A  | * | 10/1996 | Rando et al. ............. 435/238 |
| 5,962,332 | A  |   | 10/1999 | Singer et al. |
| 6,165,719 | A  |   | 12/2000 | Chandy et al. |
| 6,189,013 | B1 | * | 2/2001  | Maslyn et al. ............ 707/104.1 |
| 6,635,422 | B2 |   | 10/2003 | Keene et al. |
| 2003/0235830 | A1 | | 12/2003 | Keene et al. |

OTHER PUBLICATIONS

Feng et al., "Fragile X Mental Retardation Protein: Nucleocytoplasmic Shuttling and Association with Somatodendritic Ribosomes," The Journal of Neuroscience, 1997, vol. 17, No. 5, pp. 1539-1547.*
Schaeffer et al., "The fragile X mental retardation protein binds specifically to its mRNA via a purine quartet motif," The EMBO Journal, Sep. 3, 2001, vol. 20, No. 17, pp. 4803-4813.*
GenBank Database Accession No. AF130092, Direct Submission, Feb. 23, 1999.
Freeman, T., "High Throughput Gene Expression Screening: Its Emerging Role in Drug Discovery," Medicine Research Reviews, 2000, pp. 197-202, vol. 20(3).
Wigle, D., et al., "Mining Mouse Microarray Data," Genome Biology, 2001, pp. 1-4, vol. 2(7).
GenBank Accession No. 5524679, published Nov. 1, 2000.
GenBank Accession No. 19033971, published Mar. 1, 2002.
International Preliminary Examination Report for International Application No. PCT/US02/36861, completed on Oct. 16, 2006, mailed Nov. 16, 2006.

* cited by examiner

*Primary Examiner*—Young J Kim
(74) *Attorney, Agent, or Firm*—Alston & Bird LLP

(57) ABSTRACT

Compositions and methods for identifying and/or modulating RNA transcripts and/or genes involved in fragile X syndrome and other associated disorders are provided. In particular, RNA targets for fragile X mental retardation protein (FMRP) have been identified by a novel monoclonal antibody to FMRP and a consensus sequence for the RNA binding region has been identified. Arrays for identifying compounds, proteins, nucleotides, and the like that modulate the RNA targets or associated genes are provided. Additionally, methods for modulating RNA targets are provided.

6 Claims, 6 Drawing Sheets

| | | | | | Kd |
|---|---|---|---|---|---|
| sc1 | GUGG | AAGG | A GUGG | C UGGG | 10 nM |
| sc2 | AAGG | G UAGG | AUGG | G AUGG | 25 nM |
| sc3 | AAGG | UAGG | GUGG | UUGG | 25 nM |
| sc4 | GUGG | GUGG | UUGG | GUGG | 29 nM |
| sc5 | GAGG | AG UUGG | AAGG | A UGGG | 14 nM |
| sc6 | AAGG | UAGG | GUGG | UUGG | 31 nM |

Consensus: DWGG $N_{(0-2)}$ DWGG $N_{(0-1)}$ DWGG $N_{(0-1)}$ DWGG

FIG. 1.

Immunoprecipitation of the FMRP-mRNP Complex

```
                        SEQUENCE LISTING

<160> NUMBER OF SEQ ID NOS: 24

<210> SEQ ID NO 1
<211> LENGTH: 18
<212> TYPE: RNA
<213> ORGANISM: Artificial Sequence
<220> FEATURE:
<223> OTHER INFORMATION: conserved sequences of winning sequence SC1

<400> SEQUENCE: 1
guggaaggag uggcuggg                                                   18

<210> SEQ ID NO 2
<211> LENGTH: 18
<212> TYPE: RNA
<213> ORGANISM: Artificial Sequence
<220> FEATURE:
<223> OTHER INFORMATION: conserved sequences of winning sequence SC2

<400> SEQUENCE: 2
aaggguagga ugggaugg                                                   18

<210> SEQ ID NO 3
<211> LENGTH: 16
<212> TYPE: RNA
<213> ORGANISM: Artificial Sequence
<220> FEATURE:
<223> OTHER INFORMATION: conserved sequences of winning sequence SC3

<400> SEQUENCE: 3
aagguagggu gguugg                                                     16

<210> SEQ ID NO 4
<211> LENGTH: 16
<212> TYPE: RNA
<213> ORGANISM: Artificial Sequence
<220> FEATURE:
<223> OTHER INFORMATION: conserved sequences of winning sequence SC4

<400> SEQUENCE: 4
gugggugguu gggugg                                                     16

<210> SEQ ID NO 5
<211> LENGTH: 19
<212> TYPE: RNA
<213> ORGANISM: Artificial Sequence
<220> FEATURE:
<223> OTHER INFORMATION: conserved sequences of winning sequence SC5

<400> SEQUENCE: 5
```
gaggaguugg aaggaugggg                                                    19

<210> SEQ ID NO 6
<211> LENGTH: 16
<212> TYPE: RNA
<213> ORGANISM: Artificial Sequence
<220> FEATURE:
<223> OTHER INFORMATION: conserved sequences of winning sequence SC6

<400> SEQUENCE: 6
aagguagggu gguugg                                                        16

<210> SEQ ID NO 7
<211> LENGTH: 20
<212> TYPE: RNA
<213> ORGANISM: Artificial Sequence
<220> FEATURE:
<223> OTHER INFORMATION: consensus derived from SC1-6
<220> FEATURE:
<221> NAME/KEY: misc_feature
<222> LOCATION: (5)...(6)
<223> OTHER INFORMATION: any one or all of nucleotides 5-6 can either be
      present or absent
<220> FEATURE:
<221> NAME/KEY: misc_feature
<222> LOCATION: (11)...(11)
<223> OTHER INFORMATION: any one or all of nucleotides 11 can either be
      present or absent
<220> FEATURE:
<221> NAME/KEY: misc_feature
<222> LOCATION: (16)...(16)
<223> OTHER INFORMATION: any one or all of nucleotides 16 can either be
      present or absent
<220> FEATURE:
<221> NAME/KEY: misc_feature
<222> LOCATION: 5, 6, 11, 16
<223> OTHER INFORMATION: n = A,T,C or G

<400> SEQUENCE: 7
dwggnndwgg ndwggndwgg                                                    20

<210> SEQ ID NO 8
<211> LENGTH: 48
<212> TYPE: RNA
<213> ORGANISM: Artificial Sequence
<220> FEATURE:
<223> OTHER INFORMATION: SC1-1

<400> SEQUENCE: 8
gagcggcugc ggguguggaag gaguggcugg guugcgcacc uuggcuuc                    48

<210> SEQ ID NO 9
<211> LENGTH: 27
<212> TYPE: RNA
<213> ORGANISM: homo sapiens

<400> SEQUENCE: 9 gggggugau uggaagggag ggaggug                                             27

<210> SEQ ID NO 10
<211> LENGTH: 27
<212> TYPE: RNA
<213> ORGANISM: rattus norvegicus

<400> SEQUENCE: 10
uggcucguug guuggggugg guggcca                                            27

<210> SEQ ID NO 11

```
<211> LENGTH: 28
<212> TYPE: RNA
<213> ORGANISM: mus musculus

<400> SEQUENCE: 11 guugggguuga ggugggaag gaagguag                                              28

<210> SEQ ID NO 12
<211> LENGTH: 29
<212> TYPE: RNA
<213> ORGANISM: homo sapiens

<400> SEQUENCE: 12
ggcuacuuug gggaggugug ggaaggccu                                             29

<210> SEQ ID NO 13
<211> LENGTH: 29
<212> TYPE: RNA
<213> ORGANISM: mus musculus

<400> SEQUENCE: 13
ugucuggcag aggaaagggu ggaaagggu                                             29

<210> SEQ ID NO 14
<211> LENGTH: 33
<212> TYPE: RNA
<213> ORGANISM: homo sapiens

<400> SEQUENCE: 14
agagcgugga ggguguggaag gaguggcugc ucu                                       33

<210> SEQ ID NO 15
<211> LENGTH: 23
<212> TYPE: RNA
<213> ORGANISM: homo sapiens

<400> SEQUENCE: 15
ggggaggcag gaggaggccg agg                                                   23

<210> SEQ ID NO 16
<211> LENGTH: 34
<212> TYPE: RNA
<213> ORGANISM: homo sapiens

<400> SEQUENCE: 16
ucgcggcgcu gggagagggc ggaggggag gcgg                                        34

<210> SEQ ID NO 17
<211> LENGTH: 33
<212> TYPE: RNA
<213> ORGANISM: mus musculus

<400> SEQUENCE: 17
gacgagcgca gggaggagga gcaggagagg cag                                        33

<210> SEQ ID NO 18
<211> LENGTH: 27
<212> TYPE: RNA
<213> ORGANISM: homo sapiens

<400> SEQUENCE: 18
cccuucuagg ggaggcgggu ggggag                                                27
```

<210> SEQ ID NO 19
<211> LENGTH: 35
<212> TYPE: RNA
<213> ORGANISM: homo sapiens

<400> SEQUENCE: 19
ugugcuugcg ggaggcggug gggcauggga ggaag                          35

<210> SEQ ID NO 20
<211> LENGTH: 36
<212> TYPE: RNA
<213> ORGANISM: homo sapiens

<400> SEQUENCE: 20
cccuggccca acaggacugu gguacuaggg gcuggg                         36

<210> SEQ ID NO 21
<211> LENGTH: 26
<212> TYPE: RNA
<213> ORGANISM: homo sapiens

<400> SEQUENCE: 21
cgccuagggc aaggccgagg agaagg                                    26

<210> SEQ ID NO 22
<211> LENGTH: 27
<212> TYPE: RNA
<213> ORGANISM: mus musculus

<400> SEQUENCE: 22
uccguguggc cgauggcugg ggaaggg                                   27

<210> SEQ ID NO 23
<211> LENGTH: 41
<212> TYPE: RNA
<213> ORGANISM: Artificial Sequence
<220> FEATURE:
<223> OTHER INFORMATION: consensus sequence used to identify FMRP
      targets in unigene database
<220> FEATURE:
<221> NAME/KEY: misc_feature
<222> LOCATION: 1, 2, 3, 4, 5, 6
<223> OTHER INFORMATION: n = A, U, G, or C and forms a stem structure
      with nucleotides 41-36, respectively
<220> FEATURE:
<221> NAME/KEY: misc_feature
<222> LOCATION: 7, 8, 9, 14, 19, 24, 28, 33
<223> OTHER INFORMATION: n = A, U, G, or C and any one or all of these
      nucleotides can either be present or absent
<220> FEATURE:
<221> NAME/KEY: misc_feature
<222> LOCATION: 36, 37, 38, 39, 40, 41
<223> OTHER INFORMATION: n = A, U, G, or C and these nucleotides form a
      stem structure with nucleotides 6-1, respectivley
<220> FEATURE:
<221> NAME/KEY: misc_feature
<222> LOCATION: 1, 2, 3, 4, 5, 6, 7, 8, 9, 14, 19, 24, 28, 33, 34, 35,
      36, 37, 38, 39, 40, 41
<223> OTHER INFORMATION: n = A,U,C or G
<220> FEATURE:
<221> NAME/KEY: misc_feature
<222> LOCATION: 1, 2, 3, 4, 5, 6, 7, 8, 9, 14, 19, 24, 28, 33, 34, 35,
      36, 37, 38, 39, 40, 41
<223> OTHER INFORMATION: n = A,T,C or G

<400> SEQUENCE: 23
nnnnnnnnnd wggndwggnd wggndwgndw ggnnnnnnnn n                   41

<210> SEQ ID NO 24

```
<211> LENGTH: 47
<212> TYPE: RNA
<213> ORGANISM: Artificial Sequence
<220> FEATURE:
<223> OTHER INFORMATION: consensus sequence used to identify FMRP
      targets in polysome immunoprecipitated targets
<220> FEATURE:
<221> NAME/KEY: misc_feature
<222> LOCATION: 1,2,3,4,5
<223> OTHER INFORMATION: n = A, U, G, C and forms a stem structure with
      nucleotides 43-47, respectively
<220> FEATURE:
<221> NAME/KEY: misc_feature
<222> LOCATION: 6,7, 8, 9, 10, 11, 12, 16,17,18,19, 23, 24, 25, 26, 30,
      31, 32, 33, 37,38,39, 40, 42
<223> OTHER INFORMATION: n = A, U, G, C and any one or all of these
      nucleotides can either be present or absent
<220> FEATURE:
<221> NAME/KEY: mat_peptide
<222> LOCATION: 43, 44, 45, 46, 47
<223> OTHER INFORMATION: n = A, U, G, C and forms a stem structure with
      nucleotides 5-1, respectively
<220> FEATURE:
<221> NAME/KEY: misc_feature
<222> LOCATION: 1, 2, 3, 4, 5, 6, 7, 8, 9, 10, 11, 12, 16, 17, 18, 19,
      23, 24, 25, 26, 30, 31, 32, 33, 37, 38, 39, 40, 41, 42, 43,
      44, 45, 46, 47
<223> OTHER INFORMATION: n = A,T,C or G

<400> SEQUENCE: 24
nnnnnnnnnn nnwggnnnnw ggnnnnwggn nnnwggnnnn nnnnnnn                    47
```

METHOD AND IDENTIFICATION OF DOWNSTREAM MRNA LIGANDS TO FMRP AND THEIR ROLE IN FRAGILE X SYNDROME AND ASSOCIATED DISORDERS

FEDERALLY SPONSORED RESEARCH OR DEVELOPMENT

The research underlying this invention was supported in part with funds from National Institutes of Health Grant Nos. HD35576 and HD20521. The United States Government may have an interest in the subject matter of this invention.

FIELD OF THE INVENTION

The invention relates to methods for the identification of downstream mRNA targets of the FMRP protein and the role of these mRNAs in fragile X syndrome and associated disorders.

BACKGROUND OF THE INVENTION

The fragile X syndrome is the most common form of inherited mental retardation in humans and is estimated to afflict roughly 1 in 2500 males and 1 in 5000 females. Conditions associated with the syndrome include mild to moderate cognitive abnormalities, as well as behavioral disorders similar to autism, attention deficit disorder, obsessive-compulsive tendencies, hyperactivity, slow development of motor skills, and anxiety fear disorder. The syndrome is also frequently accompanied by seizures, by macroorchidism, and by subtle craniofacial dysmorphia.

Studies have shown that fragile X syndrome results from a deficiency of the fragile X mental retardation protein, FMRP, which is encoded by the X-linked FMR1 gene. Fragile X syndrome usually results from the transcriptional silencing of this gene brought about by the expansion and hypermethylation of a $(CGG)_n$ trinucleotide repeat in the gene's 5' untranslated region (UTR), indicating that the presence of FMRP is essential for higher cognitive function.

Cloning of the FMR1 gene led to the finding that FMRP is an RNA binding protein, with sequence analysis indicating a number of putative RNA binding domains in FMRP, specifically two tandem KH domain sequences and a C-term-inal RGG box sequence. In addition, FMRP has both a nuclear localization signal and a Rev-like export signal and is consequently believed to shuttle in and out of the nucleus. Despite this ability, the protein is largely cytoplasmic, and is incorporated into large messenger-ribonucleoprotein (mRNP) particles containing other RNA-binding proteins such as the autosomal paralogs of FMRP, FXR1P and FXR2P, which are encoded by fragile X-related genes FXR1 and FXR2, respectively. In the cytoplasm, FMRP-mRNP is normally associated with translating polyribosomes, although mutations that alter this association have been identified. A missense mutation in the second KH domain of FMRP (I304N), for example, prevents this polyribosome association and also results in a severe fragile X phenotype.

Although the exact mode of action of FMRP is not precisely understood, one unifying model for FMRP function is that the protein shuttles specific mRNAs from the nucleus to postsynaptic sites, where the mRNAs are held in a translationally inactive form until synaptic input alters FMRP activity to allow their translation. Thus, when FMRP is absent, the mRNAs normally associated with FMRP-mRNP complexes may be translationally misregulated, which, in the brain, leads to cognitive deficits.

Although FMRP has been demonstrated to be an RNA binding protein, to date there has been little success at identifying the particular RNAs or mRNAs to which FMRP binds. This inability to identify the RNAs upon which FMRP acts has left a critical gap in understanding how the absence of FMRP leads to mental retardation. There is thus a long felt need for identifying and characterizing the RNA targets of FMRP.

SUMMARY OF THE INVENTION

Compositions and methods for identifying and/or modulating RNA transcripts and/or genes involved in fragile X syndrome and other associated disorders, such as mild to moderate cognitive abnormalities, as well as behavioral similar disorders including autism, attention deficit disorder, obsessive-compulsive tendencies, hyperactivity, slow development of motor skills and anxiety fear disorder, are provided. In particular, RNA targets for FMRP have been identified by a novel monoclonal antibody to FMRP, and a consensus sequence for the RNA binding region has been identified. A series of RNA transcripts that bind FMRP are provided. The identified sequences can be assayed for a role in fragile X or other related syndromes. Arrays for identifying compounds, proteins, nucleotides, and the like that modulate the RNA targets or associated genes are provided. Additionally, methods for modulating RNA targets are provided.

BRIEF DESCRIPTION OF THE DRAWINGS

FIG. 1 shows an FMRP-selected population of RNAs containing the consensus (DWGG)4. Purified baculoviral FMRP was run on 8% SDS-PAGE, transferred to nitrocellulose, and visualized by colloidal gold staining (CG) followed by Western blotting (WB) with monoclonal antibody mAb2160 (Chemicon). Conserved sequences of the six winning sequences from RNA selection rounds 8 and 9, designated sc1-sc6 (SEQ ID NOS:1-6, respectively), are shown aligned with their consensus (SEQ ID NO:7). Kds were determined by filter binding assay. D is any nucleotide except C, W is U or A, and N is any nucleotide.

DETAILED DESCRIPTION OF THE INVENTION

FMRP Nucleic Acid Targets

Figure 2:
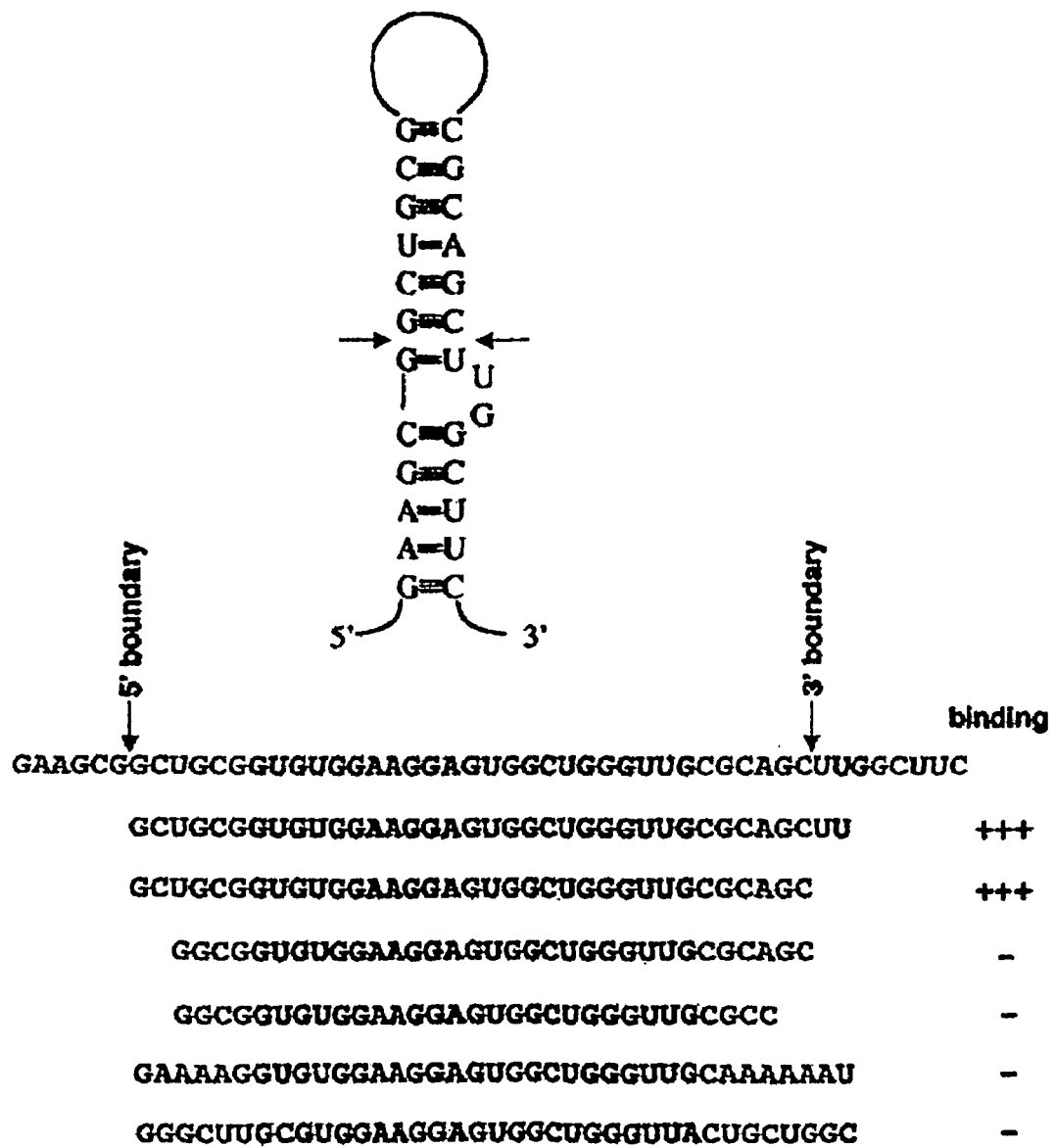
FIG. 2 shows the minimal RNA sequence bound by FMRP. Sc1 RNA (SEQ ID NO:8), end-labeled with 32P on the 3' or 5' end, was subject to limited alkaline hydrolysis (Alk hyd.), incubated with FMRP, filtered over nitrocellulose to capture RNA protein complexes, and analyzed by autoradiography. RNase T1-treated RNA generated size standards. The 5' and 3' boundaries for the interaction between sc1 and FMRP were determined. The stem loop predicted by RNase T1 protection and the 5' and 3' boundaries (indicated by arrows) of the stem are shown. RNAs were assayed for FMRP binding by filter binding (not shown).

Various FMRP nucleic acid targets are identified herein. For instance, RNA transcripts that bind FMRP have been identified and isolated. See Tables 1-5 below. As used herein, the term "FMRP" refers to the fragile X mental retardation protein, encoded by the FMR1 gene (Jin and Warren (2000) *Hum. Mol. Genet.* 9:901-908, herein incorporated by reference). The transcripts can be further assayed for a role in fragile X and/or other related syndromes. Such assay methods include, for example, translational shift assay methods such as are described below. Examples of such transcripts include the genes coding for G-protein signaling proteins, such as Sec-7 related protein (Sec7-rel. GEF sim. to KIAA0763 (112719_at)), Arf GTPase activator (Arf GTPase activator, GIT1 (97339_at)), and GAP-associated protein (GAP-assoc. p190 (96208_at)). Further examples include genes encoding proteins with functions that may be particularly involved with fragile X syndrome, such as NAP-22, MAP1B, and iGluR (iGluR, kainate-R 5γ2, Grik5 (104409_at)).

Investigations of the particular regions bound by FMRP have revealed some differences between each of the binding regions of transcripts that bind this protein. See Table 1 below and SEQ ID NOS:9-22 (setting forth the particular FMRP binding region of fourteen transcripts). In addition, the location of the binding region varies among the fourteen transcripts studied.

The present invention also provides consensus sequences for the binding region of FMRP. In one embodiment, the consensus sequence comprises sequence DWGG-N(0-2)-DWGG-N(0-1)-DWGG-N(0-1)-DWGG, where D is any nucleotide except C, W is U or A, and N is any nucleotide, with the number in parentheses after N indicating the number of occurrences of N (e.g., N(0-1) indicates either 0 or 1 nucleotides). This sequence forms a hairpin loop structure consisting of a G-quartet consensus sequence surrounded by a 6-bp stem within four nucleotides of the DWGG elements. It is recognized that minor modification may be made to the sequence as long as the ability to bind FMRP is maintained. For instance, in another embodiment, the consensus sequence comprises S6-N(0-3)DWGG-N(0-1)DWGG-N(0-1)DWG-N(0-1)DWGG-N(0-3)-S6 (S=stem), set forth as SEQ ID NO:23 (see also Table 1). Nonetheless, this sequence forms a hairpin loop structure consisting of a G-quartet consensus sequence surrounded by a stem within several nucleotides of the DWGG elements. In a further embodiment, the consensus sequence comprises S5-N(0-7)WGG-N(1-4)WGG-N(1-4)WGG-N(1-4)WGG-N(0-6)-S5, set forth as SEQ ID NO:24. This sequence also forms a hairpin loop structure consisting of a G-quartet consensus sequence surrounded by a stem within several nucleotides of WGG elements. The consensus sequences can be used to identify RNA transcripts that bind FMRP and are potential targets associated in fragile X and other related disorders.

G-quartets are nucleic acid structures in which four guanine residues are arranged in a planar conformation stabilized by Hoogsteen-type hydrogen bonds. Two to four G-quartets can stack and are stabilized by potassium and sodium but are unable to form in lithium (Williamson et al. (1989) *Cell* 59:871-880). Many variations on this structure exist including the number of nucleic acid chains involved (1, 2, or 4) and orientation of the strands relative to each other (Sen and Gilbert (1992) *Methods Enzymology* 211:191-199).

Therefore, by the term "FMRP nucleic acid target" is intended a nucleic acid molecule containing a region that ordinarily binds FMRP in a structure- and sequence-specific manner. Notably, an FMRP nucleic acid target can be altered such that it no longer binds FMRP. This binding is also altered in the presence of Li+.

The present invention also includes variants of the FMRP nucleic acid targets. Such variants, and fragments thereof differ from the nucleotide sequences shown in the figures and sequence listing. Such nucleic acid molecules may be naturally occurring, or may be constructed by recombinant DNA methods or by chemical synthesis (see below). Such non-naturally occurring variants may be made by mutagenesis techniques, including those applied to nucleic acid molecules, cells, or organisms. Accordingly, as discussed above, the variants can contain nucleotide substitutions, deletions, inversions, and insertions given the guidance in the specification as to which nucleotides are conserved or sensitive to alteration.

As used herein, two nucleic acid sequences (or a region of the sequences) are substantially homologous when the amino acid sequences are at least about 70%, 75%, 80%, 85%, 90%, 91%, 92%, 93%, 94%, 95%, 96%, 97%, 98%, 99%, or greater, homologous. To determine the percent identity of two nucleic acid sequences, the sequences are aligned for optimal comparison purposes (e.g., gaps can be introduced in one or both of a first and a second nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The nucleotides at corresponding nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (1970) *J. Mol. Biol.* 48:444-453 algorithm, which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In another embodiment, the percent identity between two nucleotide sequences is determined using the GAP program in the GCG software package (available atwww.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two nucleotide sequences can be determined using the algorithm of Meyers and Miller (1989) CABIOS 4:11-17, which has been incorporated into the ALIGN program (version 2.0), using a PAM120 weight residue table, a gap length penalty of 12 and a gap penalty of 4.

Thus, the invention encompasses isolated RNA molecules comprising an RNA consensus sequence (SEQ ID NOS:7, 23, 24) or an FMRP nucleic acid target (see, e.g., SEQ ID NOS: 9-22). The invention further comprises heterologous nucleic acid sequences. "Heterologous nucleic acid sequences" contain nucleic acid sequences not found with the sequence of interest in its natural environment or that have been synthetically (non-naturally) altered by deliberate human intervention. For instance, an FMRP nucleic acid target, FMRP binding region, or consensus sequence can be inserted into a reporter construct such that when the reporter construct is transcribed, the reporter transcript contains the FMRP nucleic acid target with the 5' UTR, the coding sequence, or the 3' UTR- The reporter transcript nucleotide sequence would be a heterologous nucleic acid sequence to the FMRP nucleic acid target.

Examples of reporter constructs are known in the art, as are methods for their construction. See Sambrook et al. (2001) *Molecular Cloning: A Laboratory Manual* (3d ed., Cold Spring Harbor Laboratory). Examples of reporter genes include Firefly luciferase, beta-glucuronidase, beta-galactosidase, cloramphenicol acetyl transferase, GFP, and the human secreted alkaline phosphatase. Such a vector has numerous uses, including screening of agents capable of modulating the translational profile of said reporter gene. See the Examples, below.

Antibodies

The present invention also encompasses antibodies and methods for their generation. In particular, because the FMRP protein sequence is highly conserved across species (that is, little variation of this sequence is seen in different species), exogenous FMRP is generally not recognized by the immune system of the inoculated animal as foreign, and therefore does not result in the satisfactory production of anti-FMRP antibodies. Therefore, one aspect of the present invention is a generalized method for producing such antibodies using FMRP-deficient FMR1 knockout mice to efficiently generate the anti-FMRP monoclonal antibodies. This method is contemplated as being generally applicable to situations in which a protein is highly conserved across species, and therefore does not generate a suitable immune response when introduced in exogenous form into an animal.

A further aspect of the invention is a monoclonal antibody that binds FMRP. As discussed, one particularly advantageous aspect of the present invention is the use of FMRP-deficient FMR1 knockout mice to efficiently generate the anti-FMRP monoclonal antibody mAb 7G1-l used in the immunoprecipitation of FMRP-containing mRNP particles described above. A cell line expressing this antibody was deposited with the American Type Culture Collection (ATCC), 10801 University Blvd., Manassas, Va., 20110-2209 on Nov. 14, 2001, and assigned Accession No. PTA-3857. This deposit will be maintained under the terms of the Budapest Treaty on Intentional Recognition of the Deposit of Microorganisms for the Purposes of Patent Procedure. It is recognized that the antibody or antibody fragments can be used. Additionally, using similar methods, antibodies that bind FMRP can be prepared. Such antibodies are useful in identifying and isolating FMRP.

As mentioned above, the FMRP target consensus sequence forms a hairpin loop structure consisting of the G-quartet consensus sequence surrounded by a 6-bp stem within four nucleotides of the DWGG elements. Such structure can be used to make monoclonal antibodies that will bind the FMRP binding region and act to modulate the RNA transcripts. Methods for making antibodies are known in the art.

Any antibody that specifically recognizes the RNA consensus sequence, including polyclonal antibodies, monoclonal antibodies, single-chain antibodies, and fragments thereof such as Fab, $F(ab')_2$, $F_v$, and other fragments which retain the antigen binding function of the parent antibody can be used in the methods of the invention. Polyclonal sera may be prepared by conventional methods. In general, a solution containing the RNA consensus antigen is first used to immunize a suitable animal, preferably a mouse, rat, rabbit, or goat. Rabbits or goats are preferred for the preparation of polyclonal sera due to the volume of serum obtainable, and the availability of labeled anti-rabbit and anti-goat antibodies. Polyclonal sera can be prepared in a transgenic animal, preferably a mouse bearing human immunoglobulin loci. Immunization can also be performed by mixing or emulsifying the antigen-containing solution in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera are obtained by bleeding the immunized animal into a glass or plastic container, incubating the blood at 25° C. for one hour, followed by incubating at 4° C. for 2-18 hours. The serum is recovered by centrifugation (e.g., 1,000×g for 10 minutes). About 20-50 ml per bleed may be obtained from rabbits.

Preferably the anti-RNA consensus antibody is monoclonal in nature. By "monoclonal antibody" is intended an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in, for example, Clackson et al. (1991) Nature 352:624-628; Marks et al. (1991) J. Mol. Biol. 222: 581-597; and U.S. Pat. No. 5,514,548.

Monoclonal antibodies can be prepared using the method of Kohler et al. (1975) Nature 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

As an alternative to the use of hybridomas, antibody can be produced in a cell line such as a CHO cell line, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Another advantage is the correct glycosylation of the antibody.

Humanized antibodies are also encompassed. By "humanized" is intended forms of antibodies that contain minimal sequence derived from non-human immunoglobulin sequences. For the most part, humanized antibodies are human immunoglobulins (recipient antibody) in which residues from a hypervariable region (also known as complementarity determining region or CDR) of the recipient are replaced by residues from a hypervariable region of a non-human species (donor antibody) such as mouse, rat, rabbit, or nonhuman primate having the desired specificity, affinity, and capacity. Humanization can be essentially performed following the method of Winter and co-workers (Jones et al. (1986) Nature 321:522-525; Riechmann et al. (1988) Nature 332: 323-327; Verhoeyen et al. (1988) Science 239:1534-1536), by substituting rodent or mutant rodent CDRs or CDR sequences for the corresponding sequences of a human antibody. See also U.S. Pat. Nos. 5,225,539; 5,585,089; 5,693,761; 5,693, 762; 5,859,205; herein incorporated by reference. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al. (1986) Nature 331:522-525; Riechmann et al. (1988) Nature 332:323-329; and Presta (1992) Curr. Op. Struct. Biol. 2:593-596; herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

The invention also provides antibody fragments. Suitable antigen-binding fragments of an antibody comprise a portion of a full-length antibody, generally the antigen-binding or variable region thereof. Examples of antibody fragments include, but are not limited to, Fab, F(ab')$_2$, and Fv fragments and single-chain antibody molecules. By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778; 5,260,203; 5,455,030; 5,856,456; herein incorporated by reference.

Screening Methods

The FMRP nucleic acid targets of the present invention and appropriate variants can be used in high-throughput screens to assay candidate compounds for the ability to modulate the translational profile of the target nucleic acid in a wild-type or fragile X cell (see below). Compounds can be identified that increase or decrease the translational profile. Such modulatory methods can be performed in vitro (e.g., by culturing a cell with the agent) or, alternatively, in vivo (e.g., by administering the agent to a subject).

For instance, a reporter construct containing an FMRP nucleic acid target can be transfected into a cell having a wild-type or fragile X phenotype. The assay includes the steps of combining the cell with a candidate compound under conditions that allow the FMRP nucleic acid target to interact with the compound, and to detect the effect of said contact upon the translation profile of the target. The effect, if any, can be determined by polyribosome assay (see below) or simply by assaying for the reporter gene and comparing its translation to that of a cell that has not been contacted by said compound.

Test compounds can be obtained using approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds maybe presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner, U.S. Pat. No. '409), plasmids (Cull et al. (1992) *Proc. Natl. Acad. Sci. USA* 89:1865-1869), or on phage (Scott and Smith (1990) *Science* 249:386-390); (Devlin (1990) *Science* 249:404-406); (Cwirla et al. (1990) *Proc. Natl. Acad. Sci.* 97:6378-6382; Felici (1991) *J. Mol. Biol.* 222:301-310; Ladner supra.

Candidate compounds include, for example, 1) peptides such as soluble peptides, including Ig-tailed fusion peptides and members of random peptide libraries (see, e.g., Lam et al. (1991) *Nature* 354:82-84; Houghten et al. (1991) *Nature* 354:84-86), and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767-778); 3) antibodies (e.g., polyclonal, monoclonal, humanized, anti-idiotypic, chimeric, and single-chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

In accordance with the methods of the present invention, at least one candidate compound as defined elsewhere herein is used to promote a positive response with respect to a fragile X cell. By "positive therapeutic response" is intended an improvement in the disorder, syndrome, symptoms, or translational profile associated with the disorder.

By "therapeutically effective dose or amount" is intended an amount of a compound that, when administered, brings about a positive therapeutic response with respect to treatment of a patient with a fragile X or associated disorder. Administration of the pharmaceutical composition comprising the therapeutically effective dose or amount can be achieved using any acceptable administration method known in the art. Preferably the pharmaceutical composition comprising the compound thereof is administered intravenously, preferably by infusion over a period of about 1 to about 24 hours, more preferably over about 1 to about 16 hours, even more preferably over about 2 to about 10 hours, still more preferably over about 4 to about 8 hours, depending upon the antibody being administered. Subsequent infusions may be administered over a period of about 1 to about 6 hours, preferably about 1 to about 4 hours, more preferably about 1 to about 3 hours.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates, and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

The compounds are typically provided by standard technique within a pharmaceutically acceptable buffer, for example, sterile saline, sterile buffered water, propylene glycol, combinations of the foregoing, etc. Methods for preparing parenterally administrable agents are described in *Remington's Pharmaceutical Sciences* (18$^{th}$ ed.; Mack Publishing Company, Eaton, Pa., 1990), herein incorporated by reference. See also, for example, WO 98/56418, which describes stabilized antibody pharmaceutical formulations suitable for use in the methods of the present invention.

The amount of at least one compound to be administered is readily determined by one of ordinary skill in the art without undue experimentation. Factors influencing the mode of administration and the respective amount include, but are not limited to, the severity of the disorder, and the age, height, weight, health, and physical condition of the individual undergoing therapy. The dose of the compound thereof to be administered is in the range from about 0.003 mg/kg to about 50 mg/kg, preferably in the range of 0.01 mg/kg to about 40 mg/kg.

Genes/transcripts identified herein as involved in fragile X and related disorders can be used to identify compounds, proteins, nucleotides, small molecules, and the like, that are useful in modulating the genes and/or transcripts or in altering translation of the transcripts, and thus, can be used to treat such syndromes. Additional assays are available for identifying such compositions as described below. As noted above, antibodies to the RNA consensus region can be used to modulate such transcripts.

Methods of Identifying FMRP Nucleic Acid Targets

The present invention contemplates FMRPs obtained from a variety of organisms, including humans and mice, and from a variety of tissues within any particular organism, including, but not limited to, brain tissue.

In one embodiment, the present invention is directed to identifying the RNA ligands or targets of FMRP, that is, RNA molecules that bind FMRP or otherwise physically interact with FMRP. Such molecules are contemplated to include molecules of biological significance, for example mRNAs whose aberrant expression is associated with fragile X syndrome, as well as other RNAs that bind FMRP but do not necessarily exhibit biological effects. Such RNAs include, for example, the small RNA molecules used in the RNA selection experiments of Examples 1 and 2 below to define the RNA G-quartet motif specifically recognized by FMRP.

In one particular embodiment, the present invention provides a method for identifying RNA targets of FMRP using in vitro RNA selection. Thus as described in Examples 1 and 2 below, multiple rounds of selection of synthetic RNAs can be used to identify a consensus RNA sequence present in the synthetic RNAs bound by FMRP. Here, the consensus sequence identified is the G-quartet consensus sequence DWGG-N(0-2)-DWGG-N(0-1)-DWGG-N(0-1)-DWGG, where D is any nucleotide except C, W is U or A, and N is any nucleotide, with the number in parentheses after N indicating the number of occurrences of N (e.g., N(0-1) indicates either 0 or 1 nucleotides). See SEQ ID NO:7. Other methods described in Examples 1 and 2 can be used to show that high affinity binding of this G-quartet consensus sequence by FMRP occurs when the consensus sequence is presented in a stem-loop structure, allowing the definition of a consensus structure of the G-quartet consensus sequence (see FIGS. 2 and 4, and Table 1). As used herein, the term "RNA G-quartet structure" refers to the loop portion of this consensus structure. Note that the RNA G-quartet structure is bordered by a stem region.

The present invention also provides an in silico method for identifying RNAs containing the RNA G-quartet structure, as described in Example 3 below. In one embodiment of this method, a sequence database is searched for sequences containing the RNA G-quartet structure using the appropriate search algorithm. In Example 3, for example, the UniGene database of sequences was searched for the appropriate sequences using RNABob. However, the method is contemplated to include other databases of sequences, including other transcript databases, and other search algorithms such as would be known to the skilled artisan. The method may also include additional steps for reducing the number of sequences to be considered, both in silico and in vivo, as are presented in Example 3 below.

Another method of identifying RNAs containing the RNA G-quartet structure contemplated in the present invention is the identification of such RNAs by hybridization methods. The skilled artisan would know, for example, that the G-quartet consensus sequence can be used to design probes for the identification of hybridizing sequences, and that these sequences can be further examined by a variety of methods for the presence of the appropriate hairpin structure. The skilled artisan would also understand that an additional form of hybridization procedure would be to use sequences complementary to the G-quartet consensus sequence for RT-PCR experiments to amplify RNAs containing the G-quartet consensus sequence, and that such identified sequences could then be further examined for the presence of the appropriate hairpin structure.

A variety of hybridization conditions are contemplated in the present invention. For example, sequences that hybridize under stringent conditions to the RNA G-quartet consensus sequence are encompassed by the present invention. As used herein, the term "hybridizes under stringent conditions" is intended to describe conditions for hybridization and washing under which nucleotide sequences typically remain hybridized to each other. Such stringent conditions are known to those skilled in the art and can be found in *Current Protocols in Molecular Biology* (John Wiley & Sons, N.Y., (1989), 6.3.1-6.3.6. A preferred example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions is hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5 M Sodium Phosphate, 7% SDS at 65° C., followed by one or more washes at 0.2×SSC, 1% SDS at 65° C. Preferably, an isolated nucleic acid molecule of the invention that hybridizes under stringent conditions to a sequence disclosed herein corresponds to a naturally occurring nucleic acid molecule. As used herein, a "naturally occurring" nucleic acid molecule refers to an RNA or DNA molecule having a nucleotide sequence that occurs in nature (e.g., encodes a natural protein).

A different method for identifying RNA targets of FMRP is by immunoprecipitation of FMRP-containing mRNP particles followed by identification of the RNAs present in the immunoprecipitate by, for example, microarray analysis, as is described in Examples 11 and 12 below. Although microarray analysis is presented as one embodiment of the present invention, other methods of identification of the RNAs present in the immunoprecipitate that would be known to the skilled artisan are contemplated.

A second aspect of the present invention is directed to the characterization of the protein binding properties of the RNA G-quartet structure, or of RNAs containing this structure. The filter binding methods described in Example 2, for example, can be used to assay the binding to RNAs containing the RNA G-quartet structure of a variety of proteins, including FMRPs, proteins related to FMRP such as FXR1P or FXR2P, proteins containing the RGG box, proteins present in the FMRP-mRNP complex, or test proteins with an unknown binding affinity for RNAs containing the RNA G-quartet structure. In addition to filter binding, other methods of measuring binding are also contemplated. For example, electrophoretic mobility shift methods such as those provided in Example 1 may also be used to determine the fractions of bound versus unbound RNA, as may other methods known to one of ordinary skill.

The protein binding methods discussed above are specifically contemplated to include methods for determining the binding of the RNA G-quartet structure, or of RNAs containing this structure, to more than one protein. For example, these methods may be used to characterize the binding of the RNAs discussed into mRNP particles containing, for example, FMRP, FXR1P, FXR2P, etc., and the binding of any particular RNA to one or more of these proteins is contemplated herein. This method is also contemplated to include the binding of the RNA G-quartet structure, or of RNAs containing this structure, to ribosomes or polyribosomes.

A third aspect of the present invention relates to the differential binding or association of the RNA G-quartet structure, or of RNAs containing this structure (i.e., of FMRP-binding RNA), to polyribosomes; that is, the translational shift assay described in Example 14. This assay is expected to provide information on a key aspect of fragile X syndrome, namely the translational misregulation of FMRP-binding mRNAs discussed above, and may also be used to assay the ability of compounds to reduce or eliminate this effect, as will be discussed below.

In one embodiment of the translational shift assay (Example 14), the amount of FMRP-binding RNA that binds to polyribosomes where FMRP is present is compared to the amount of FMRP-binding RNA that binds in the absence of FMRP. Thus this assay provides a method for measuring one biological consequence of the absence of FMRP on an FMRP-binding RNA. In Example 14, the absence of FMRP was obtained via the use of polyribosomes obtained from patients with fragile X syndrome. However, the invention specifically contemplates other ways of removing or inactivating FMRP, for example the use of a monclonal antibody against FMRP, such as mAb 7G1-1 described above.

The translational shift method also encompasses binding modulated by the presence or absence of a test compound. That is, as generally applied, the method involves comparing the binding of an FMRP-binding RNA to polysomes in the presence of the test compound (or compounds) with binding to polysomes in the absence of the compound (or compounds). Test compounds encompassed by the invention include other proteins comprising the mRNP complex, such as FXR1P and FXR2P, as well as other proteins or molecules such as antibodies that may be expected to modulate the differential binding of the FMRP-binding RNA, as well as small molecules, for example small molecules such as might be identified by the combinatorial screening of simple organic chemical libraries.

The translational shift assay may be used to study the translational shift of an individual FMRP-binding RNA, or to study the shift exhibited in an entire population of such RNAs. The study of a particular RNA may be important for those RNAs thought to have particular significance in fragile X syndrome or a related disorder. Batch population studies are of value because they do not require a precise knowledge of the mRNAs or encoded proteins that are most compromised in fragile X syndrome or in a related disorder. In either case, the amount of each RNA present may be determined by a variety of methods known to the skilled artisan, including microarray analysis, RT-PCR, hybridization, or the like, with the use of microarray analysis specifically provided in Example 14. Furthermore, the method is specifically contemplated to encompass both differential increases and decreases in translation.

A fourth aspect of the present invention is directed to methods for assaying test compounds for their ability to modulate the molecular events relating to fragile X syndrome or associate disorders. For example, the filter binding assays described above for assaying the protein binding properties of FMRP-binding RNAs may be used to assay test compounds for their ability to interfere with this RNA-protein binding process. Alternatively, these filter binding assays may be used to determine whether a test compound itself binds the RNA G-quartet structure, or binds RNAs containing this structure. Compounds exhibiting such binding may mimic the properties of FMRP, and might therefore serve as therapeutic replacement molecules for FMRP.

Another method for assaying test compounds for their modulatory ability involves the use of the translational shift assays discussed above. Specifically, such assays may be used to determine whether the amount of FMRP-binding RNA that binds to polyribosomes is modulated by the presence or absence of the test compound in the same way that FMRP modulates such binding. It is anticipated that compounds that mimic the profiles observed with FMRP may have desirable therapeutic properties in the treatment of fragile X syndrome.

In all of the above methods, it will be particularly advantageous to use the mRNAs identified as containing the RNA G-quartet structure or otherwise binding to FMRP. Within this group of sequences it may be of interest to study particular groupings of sequences, for example the genes coding for G-protein signaling proteins (e.g., Sec 7-related protein, Arf GTPase activator, and GAP-associated protein), or genes encoding proteins with functions that may be particularly involved with fragile X syndrome (e.g., NAP-22, MAP1B, and iGluR). Particular groupings of sequences might also include those involved in maintaining proper synaptic function, mediating neuronal development, or in craniofacial development as are discussed in, for example, Examples 8, 18, and 20 below. Other groupings defined by common structural or functional properties would be known to the skilled artisan.

The above mRNAs may be used in their natural form, or as fragments thereof. As such, these nucleic acid molecule of the invention may include only a portion of the nucleic acid sequence of the full length RNA or a portion of the DNA encoding said full length sequence. Such a nucleic acid molecule can include a fragment that can be used as a probe or primer or a fragment encoding a portion of the protein encoded by the mRNA, e.g., an immunogenic or biologically active portion. A nucleic acid fragment can include a sequence corresponding to a domain, region, or functional site described herein. A nucleic acid fragment can also include one or more domain, region, or functional site described herein. As discussed above, variants of the mRNAs above are also contemplated.

It is contemplated that these mRNAs may be particularly useful when they are operably linked to a reporter sequence, which allows for their detection. That is, an identified mRNA nucleotide sequence, or variant thereof (such as the protein-encoding region, an RNA G-quartet structure-containing region, or the region defined as encoding a functional domain or domains) may be operably linked to a nucleotide sequence that functions as a reporter.

By "operably linked" is intended a functional linkage between a nucleic acid sequence and a second sequence. Generally, operably linked means that the nucleic acid sequences being linked are contiguous and, where necessary to join two protein coding regions, contiguous and in the same reading frame.

It is further contemplated that any of the sequences identified as binding sequences may be modulated in vivo to alleviate or otherwise alter the symptoms or other manifestations of fragile X syndrome or associated disorder. Such modulation may be of an individual mRNA sequence, or en masse. Modulation of an individual sequence may be appropriate for a sequence that is of particular consequence to fragile X syndrome or to a related disorder. As contemplated herein, modulation may be accomplished by administering to a patient a chemical such as a small molecule, peptide, or polypeptide, that changes the expression of the gene. Modulation may also be accomplished by administration of genetically engineered cells producing the modulating agent.

The following nonlimiting, illustrative examples are presented.

EXPERIMENTAL

A. Identification of MRNAS Bound by FMRP by RNA Selection

Example 1

In vitro RNA Selection with FMRP

Baculoviral histidine-tagged FMRP was purified by sequential metal-chelating and polyribo-G affinity chromatographies (not shown). This FMRP was bound to a nickel-Sepharose column and used to bind a pool of $^{32}$P-UTP labeled 96-mer RNAs containing 52 bases of random sequence. FMRP was eluted with imidazole and co-eluting RNAs were pooled, amplified by reverse transcription-PCR, and retranscribed for subsequent RNA selection. Clones were sequenced following the $7^{th}$-$9^{th}$ rounds of selection.

Sequencing 39 clones from the $8^{th}$ and $9^{th}$ rounds revealed only 6 different species of cDNA, and by the 9 th round two of the 6 clones made up 75% of the pool. Round nine clones contained 5 unique sequences, whose frequency varied from 1/24 to 9/24 (not shown, sc1-5), and round eight contained one additional clone (sc6). Examination of these six sequences revealed a common sequence motif of DWGG-N (0-2)-DWGG-N(0-1)-DWGG-N(0-1)-DWGG (FIG. 1).

In order to determine the binding affinity of FMRP for each RNA species, nitrocellulose filter binding assays were performed with $^{32}$P-UTP-labelled RNAs (not shown). The RNA with the best affinity for FMRP, sc1, has a Kd of 10 nM (FIG. 1). This affinity is in the low nanomolar range, consistent with the affinities of many RNA-binding proteins for their in vivo targets.

To assess whether FMRP interacts directly with sc1, an electrophoretic mobility shift assay was performed. FMRP shifted the migration of sc1 RNA to a more slowly migrating band (not shown). An irrelevant KH-type RNA binding protein, Nova, did not shift sc1 RNA, and the migration of an irrelevant RNA was not shifted by FMRP (not shown). Addition of a monoclonal antibody to FMRP supershifted the bands (not shown), while an irrelevant monoclonal did not.

In order to determine the minimal RNA sequence necessary for high affinity FMRP binding, the interaction with a minimal RNA corresponding to the sc1 conserved element was examined, though any binding by filter binding was not detected (data not shown). This suggested that additional sequences outside the conserved element were essential for binding, and led to the mapping of the 5' and 3' boundaries of the RNA that interacted with FMRP. Full-length sc1 RNA was end-labeled with $^{32}$P and subjected to mild alkaline hydrolysis to generate a ladder of 3' or 5' labeled RNAs (not shown). These RNAs were bound to FMRP, filtered through nitrocellulose to capture FMRP-RNA complexes, eluted from the filter and analyzed by denaturing PAGE. In this way, the 5' and 3' boundaries for FMRP binding to sc1 was mapped to nucleotides 23-57, respectively (FIG. 2).

While generating RNAse T1 digested sc1 fragments as size standards in the boundary mapping experiment it was noted that two domains in sc1 were protected from RNAse T1, even in 7 M urea at 50° C. (not shown). The protected domain identified by 5' labeling can be predicted to form a stable stem with the domain protected using 3' labeling (FIG. 2). The 5' and 3' boundaries map near the middle of the stem suggesting that a minimal 5-6 nucleotide stem is necessary for FMRP binding.

In order to confirm the boundary mapping results, truncated RNAs were transcribed in vitro and tested for FMRP binding by filter binding assay (not shown). These results demonstrated that for this RNA species, a 5-6 nucleotide stem was sufficient for high affinity FMRP binding; truncating the stem inside the boundaries destroyed binding. In order to test the importance of the stem, mutants were generated in which the stem sequence was scrambled or replaced with adenine residues, both of which abrogated FMRP binding by over three orders of magnitude (data not shown).

Figure 3:
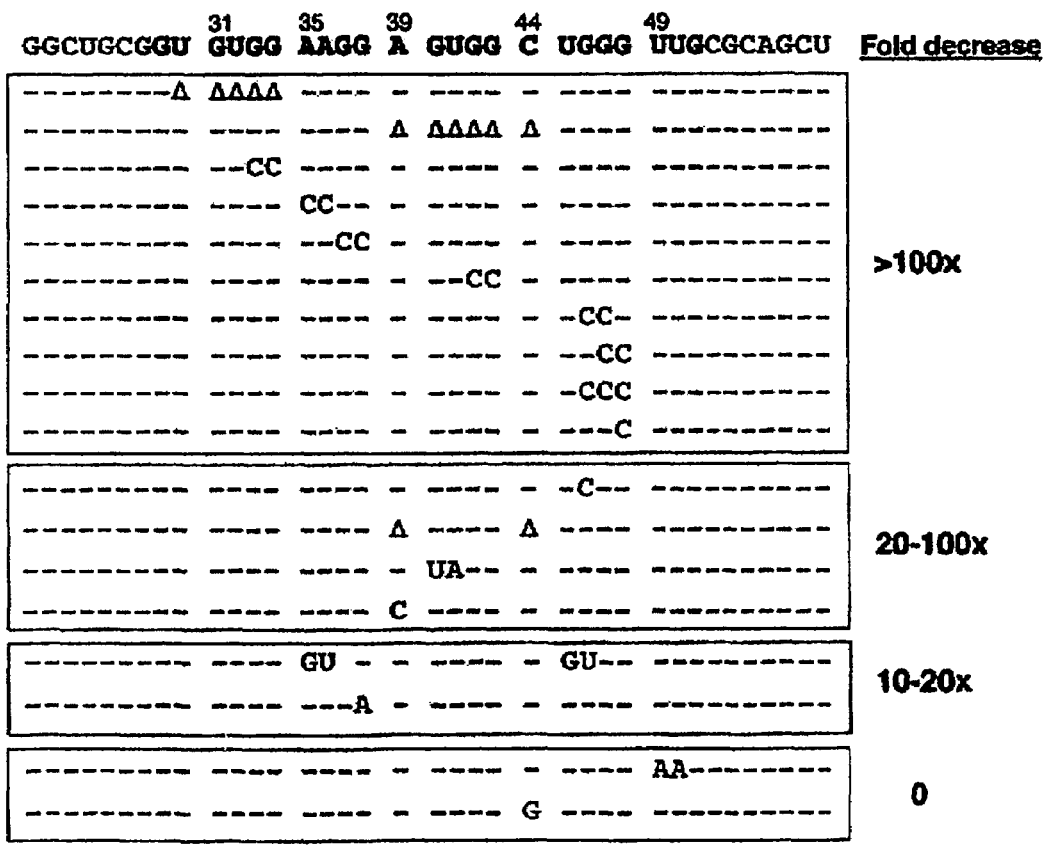
FIG. 3 shows results of mutational analysis of sc1 RNA. Mutations in truncated sc1 RNAs (bp 15-8) were assayed for FMRP affinity by filter binding assay. The first seven and the final seven nucleotides at the top of the figure (regular font) are involved in stem formation, loop sequences (29-51) are in bold, mutations are shown in the table, unchanged bases are shown by a dash, and deletions are shown as Δ. Reductions in FMRP binding are indicated relative to sc1. These results were duplicated with a smaller sc1 truncation (bp 13-58; data not shown).

In order to test the determined consensus, a number of point mutations and internal deletions were generated in the conserved sequence motif, and binding of these RNAs tested by filter binding assay (FIG. 3). Two sets of mutants were tested with the same results: one beginning at the 5' end of the sc1 and ending with the 3' nucleotide shown in FIG. 3 (72 mers) and a second beginning with an internal primer and ending with the same 3' sequence (45 mers).

The RNA mutations that had the most severe effects on FMRP binding (<1% wild-type sc1 binding) resulted from changing or deleting the paired G's (G33/G34, G37/G38, G42/G43, and G47/G48). In addition, mutating two As (A35/A36) to a pair of Cs resulted in a severe decrease in FMRP binding; this mutation may have abrogated a sequence-specific interaction or altered the RNA secondary structure (see below). Mutation or deletion of the "spacer" nucleotide A39 resulted in a marked decrease (1-5% wild-type sc1 binding) in FMRP affinity. Mutation of the spacer nucleotide C44 from a C to G had no effect. Interestingly, changing G40/U41 to a UA resulted in a significant decrease in binding, which was unexpected as the consensus is maintained. Mutations that had only minimal effects on RNA binding affinity (less than 20 fold) included changing G38 to an A, (discussed below), U49/U50 to A49/A50 (nucleotides that lie between the conserved bases and the stem), and changing all 4 DWGG elements to GUGG.

Figure 4:
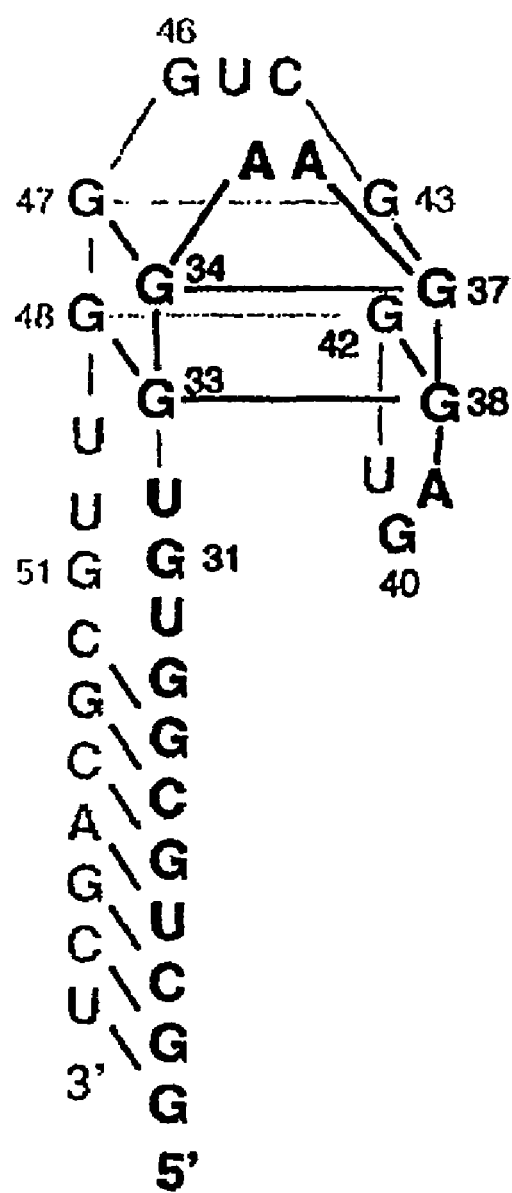
FIG. 4 shows a schematic representation of the proposed structure of sc1 RNA, which forms an intramolecular G-quartet. The proposed Hoogsteen base-paired Gs and a stem are shown. Nucleotide numbers correspond to FIG. 3. See nucleotides 6-42 of SEQ ID NO:8.

The presence of four sets of paired Gs that are crucial for FMRP binding suggested a structure in which the loop present in the stable stem-loop of sc1 folds into an intramolecular G-quartet (FIG. 4). G-quartets are nucleic acid structures in which four guanine residues are arranged in a planar conformation stabilized by Hoogsteen-type hydrogen bonds. Two to four G-quartets can stack and are stabilized by potassium and sodium but are unable to form in lithium (Williamson et al. (1989) *Cell* 59:871-880). Many variations on this structure exist including the number of nucleic acid chains involved (1, 2, or 4) and orientation of the strands relative to each other (Sen and Gilbert (1992) *Methods Enzymnology* 211:191-199). In order to test whether formation of a G-quartet is necessary for FMRP binding, sc1 binding in K$^+$ and Li$^+$ buffers was assayed. FMRP-sc1 binding was abrogated in Li$^+$ buffer, while binding to a control RNA, sc11, which binds FMRP in a different manner (see below), was unaffected by the substitution of Li$^+$ for K$^+$ in the binding buffer.

To further test whether sc1 folds into a G-quartet, RNAse T1 digestion was performed (not shown). Under the reaction conditions used, RNAse T1 cleaves RNA specifically on the 3' side of unpaired guanines. Each of the paired Gs in sc1

(designated $G_4$) were protected from RNAse T1 digestion in $K^+$ buffer relative to $Li^+$ buffer, suggesting that these nucleotides are base-paired in the G-quartet structure proposed. G31, G40, and G46 are protected from cleavage in $K^+$ buffer but are not predicted to take part in the G-quartet. These bases may be base-paired with other bases present in the 96mer RNA in conventional Watson-Crick interactions or may be sterically hindered from digestion due the compact folding of the RNA and the relatively large size of RNAse T1 (Ehresmann et al. (1987) *Nucleic Acids Res.* 15:9109-9128). In contrast to the loop sequence Gs proposed to base pair in a G-quartet, the G nucleotides present in the sc1 stem are protected from digestion by base pairing in both buffers. Moreover, a control RNA, sc11, is equally susceptible to RNAse T1 in $K^+$ or $Li^+$.

To confirm these results, a time course of RNAse T1 digestion was performed with sc1 in $K^+$ vs. $Li^+$ buffers in an independent experiment. At all time points the paired Gs are protected from T1 digestion in $K^+$ relative to $Li^+$. Gs 3' to G71 are cleaved equally well under both conditions (not shown). Substitution of G38 to an A had little effect, consistent with the observation that RNA G-quartets may be able to form using G-A Hoogsteen base pairs (Awang and Sen (1993) *Biochemistry* 32:11453-11457); Sundquist and Heaphy (1993) *Proc. Natl. Acad. Sci. USA* 90:3393-3397; Lee (1990) *Nucleic Acids Res.* 18:6057-6060). Taken together, these results demonstrate that FMRP binds sc1 in a manner that is dependent on the RNA folding into a G-quartet.

Example 2

Identification of the FMRP Domain that Binds the sc1 G-Quartet

In order to determine the domains of FMRP responsible for binding to sc1 the I304N mutation in the KH2 domain was generated and the equivalent mutation in the KH1 domain of full-length FMRP was generated, singly or in combination. These mutant proteins bound sc1 nearly as well as wild-type FMRP, suggesting that sc1 RNA binds FMRP in a KH domain-independent manner (not shown). Testing the isolated N- and C-termini of FMRP revealed that all the sc1 binding activity is in the C-terminal domain of FMRP, distal to the KH domains (not shown).

Deletions of the C-terminus were produced in the pET system and assayed for sc1 binding (not shown). Assessment of a series of mutant proteins revealed that the RGG box alone had an affinity of 10 nM for sc1 RNA, which was indistinguishable from the affinity of full-length FMRP. Because RGG boxes have been suggested to be nonspecific RNA-binding domains, RGG binding to a number of control RNAs was assessed (not shown). Mutation of the GG pair in either the second or third DWGG elements decreased binding to the RGG box by at least three orders of magnitude, comparable to results obtained with full-length FMRP (FIG. 3). In addition, sc11, a 230 bp fragment of 28S rRNA, or the starting pool of random 96-mer RNAs from which sc1 was selected were assayed for binding to the FMRP RGG box, and all similarly showed no significant binding affinity (Kd>5 µM; data not shown). These results confirm that the FMRP RGG box binds with high affinity to RNA in a structure- and sequence-specific manner.

Example 3

Identification of In Vitro-Selected Clones that Bind the KH2 Domain

The sequencing of 24 clones from the 7th round revealed seven additional RNAs, all which bound full-length FMRP with high affinity (Kd's~25-55 nM). Filter binding analysis of the interaction between the C-terminus and these RNAs demonstrated that two were bound very poorly by the RGG box (sc10 and sc11, data not shown). Sc10 and sc11 were used in binding assays with wild-type full-length FMRP and I304N KH2 mutant protein. While sc1 was bound equally well by both proteins, sc10 and sc11 binding were significantly abrogated by the I304N KH2 mutation. To confirm the interaction between one RNA and the KH2 domain, isolated KH domain fusion proteins were assayed for sc11 binding. While the paired KH1+KH2 domains bound sc11 with the highest affinity (Kd~50 nM), KH2 alone also bound sc11 with high affinity (Kd~10 nM). The I304N mutation in the KH2 domain severely abrogated sc11 binding (Kd>5 µM). KH1 alone did not bind sc11 detectably, although it is noted that there is no positive control in this experiment to confirm that KH1 is folded correctly under these conditions. The six additional $7^{th}$ round RNA clones were assayed for KH1 binding and none bound at up to 1 µM protein (data not shown). These data demonstrate that sc11 RNA interacts with the FMRP KH2 domain in an I304-dependent manner, with an affinity perhaps 2-5 fold less than for the full-length protein. While one cannot exclude a contribution to binding affinity from other regions of FMRP, it is noted that the RGG box itself does not bind sc11 (Kd>5 µM; data not shown).

Filter binding assays with sc10 confirm that it is also bound by the KH2 domain (data not shown). The sequences of sc10 and sc11 show many similarities.

Example 3

FMRP RNA Targets Predicted from RNA Selection mRNA transcripts that might be bound by FMRP were identified by searching UniGene for the G-quartet consensus sequence surrounded by a 6-bp stem within four nucleotides of the DWGG elements using RNABob, a program capable of searching for both structural and sequence-specific elements (see www.genetics.wustil.edu/eddy/software; Gautheret et al. (1990) *Comput. Appl. Biosci.* 6:321-331). RNABob predicted 71 FMRP binding sites from the UniGene database. These sequences were folded by mfold version 3.1 (Matthews et al. (1999) *J. Mol. Biol.* 288:911-940) and those sequences that had competing internal stems were discarded. Of the 31 remaining targets likely to fold into G-quartets, 12 were assayed for FMRP binding (Table 1, below). Of these 12 candidates, 6 bound to FMRP with affinities ranging from Kd 75 nM to 467 nM, while 6 did not bind (Kd>1.2 µM).

TABLE 1

FMRP RNA Targets

| mRNA | Kd nM | Location of Target | G Quartet | ID | Alteration in Fra(X) Polysomes | GenBank Accession Code |
|---|---|---|---|---|---|---|
| 1<br>Semaphorin 3F, human<br>GGGGGGTGATTGGAAGGGAGGGAGGTG | 75 | 3'UTR | Yes | Uni Gene | Decreased | NM_004186 |
| 2<br>Potassium Channel Kv3.1, rat<br>TGGCTCGTTGGTTGGGGTGGGTGGCCA | 113 | 5'UTR | Yes | Uni Gene | Unchanged | NM_012856 |
| 3<br>Arginine vasopressin receptor, V1a, mouse<br>GTTGGGTTGAGGGTGGGAAGGAAGGTAG | 156 | 3'UTR | Yes | Uni Gene | Decreased | D49730 |
| 4<br>Srm tyrosine kinase, human<br>GGCTACTTTGGGGAGGTGTGGGAAGGCCT | 171 | Coding | Yes | Uni Gene | N.D. | AL121829 |
| 5<br>Histone H4, mouse<br>TGTCTGGCAGAGGAAAGGGTGGAAAGGGT | 190 | Coding | Yes | Uni Gene | N.D. | V00753 |
| 6<br>Transcription differentiation inhibitor, ID3, human<br>AGAGCGTGGAGGTGTGGAAGGAGTGGCTGCTCT | 467 | 3'UTR | Yes | Uni Gene | Unchanged | NM_002167 |
| 7<br>Guanine nucleotide exchange factor, human<br>GGGGAGGCAGGAGGAGGCCGAGG | 322 | 3'UTR | Yes | Co-IP | N.D. | NM_014869 |
| 8<br>MAP1B, transcript 1, human<br>TCGCGGCGCTGGGAGAGGGCGGAGGGGAGGCGG | 505 | 5'UTR | Yes | Polysome & Co-IP | Increased | NM_005909 |
| 9<br>Msx2-interacting nuclear protein (Mint), mouse<br>GACGAGCGCAGGGAGGAGGAGCAGGAGAGGCAG | 462 | Coding | Yes | Polysome & Co-IP | Increased | NM_019763 |
| 10<br>GT334/TMEM1/EHOC-1, site 1, human<br>CCCTTCTAGGGGAGGCGGGTGGGGAG | 505 | 3'UTR | Yes | Polysome & Co-IP | Increased | U61500 |
| 11<br>GT334/TMEM1/EHOC-1, site 2, human<br>TGTGCTTGCGGGAGGCGGTGGGGCATGGGAGGAAG | 425 | 3'UTR | N.D. | Polysome & Co-IP | Increased | U61500 |
| 12<br>Munc 13, mammalian homolog of unc13, human<br>CCCTGGCCCAACAGGACTGTGGTACTAGGGGCTGGG | 194 | 3'UTR | N.D. | Polysome & Co-IP | Decreased | AF020202 |
| 13<br>Neuronal acidic membrane protein, NAP-22, human<br>CGCCTAGGGCAAGGCCGAGGAGAAGG | 599 | Coding | N.D. | Polysome & Co-IP | Decreased | AI214799 |

TABLE 1-continued

FMRP RNA Targets

| mRNA | Kd nM | Location of Target | G Quartet | ID | Alteration in Fra(X) Polysomes | GenBank Accession Code |
|---|---|---|---|---|---|---|
| 14<br>Rab6 interacting protein,<br>KIAA 1091, mouse<br>TCCGTGTGGCCGATGGCTGGGGAAGGG | 275 | Coding | N.D. | Polysome & Co-IP | Decreased | AJ245569 |

Table 1. RNA targets were identified through RNABob searching (UniGene), in vivo co-IP/gene-chip analysis of targets (Co-IP), or through analysis of targets altered in their polysome distribution in fragile X patient cells (Polysome/IP). Kds were determined by filter binding assay, using both full-length FMRP and the C-terminal RGG box. G-quartet-dependent binding was assessed by measuring $Li^+$ sensitive FMRP binding (the first ten RNAs listed) and by mutation of Hoogsteen-paired Gs (the first six RNAs listed). Of 11 Polysome/IP targets tested, four did not bind FMRP and are not listed. UniGene was searched with S6-N(0-3)DWGG-N(0-1)DWGG-N(0-1)DWG-N(0-1)DWGG-N(0-3)-S6(S = stem), SEQ ID NO:23, and polysome/IP targets using (S5-N(0-7)WGG-N(1-4)WGG-N(1-4)WGG-N(1-4)WGG-N(0-6)-S5, SEQ ID NO:24. N.D. = not determined. The RNA corresponding to entries 1-14 are set forth in SEQ ID NOS:9-22, respectively.

FMRP binding to RNAs found to be candidate targets by immunoprecipitation has also been assessed. See Examples 11-21 below. The RNA found to be most enriched in FMRP immunoprecipitations from brain (Sec7-related transcript KIAA0763, a guanine nucleotide exchange factor [Sec7-related GEF]) was assessed. In addition, RNAs that co-immunoprecipitate with FMRP from brain that are also altered in their polysome distribution in lymphoblastoid cell lines derived from Fragile X patients (see below) were examined. These RNAs were again searched using the RNABob algorithm for FMRP binding sites, identifying 11 elements that were tested by filter binding assay for direct FMRP interaction. GEF mRNA bound FMRP with an affinity of 322 nM. Of the 11 polysome-altered targets, 7 bound with affinity to FMRP ranging from 194 nm to 599 nM, while 4 had undetectable binding (Table 1).

To assess whether the RNAs listed in Table 1 bound FMRP in a G-quartet dependent manner, binding in the presence of $Li^+$ versus $K^+$ was assessed, and mutants in which the Hoogsteen paired Gs were changed to Cs were generated. In each case tested (10 targets assayed in the presence of $Li^+$, and 6 mutated RNA targets, see Table 1), FMRP binding was abrogated. For instance, the binding of the mouse guanine nucleotide exchange factor (Sec7-related GEF) RNA was assayed for FMRP binding in $K^+$ vs. $Li^+$, and an anti-sense version of the transcript was assayed in $K^+$. Only the sense transcript showed appreciable binding in $K^+$, and its binding was abrogated in $Li^+$. These results were duplicated using the C terminus of FMRP (data not shown).

These results demonstrate that FMRP binds with high affinity to G-quartet elements in these transcripts, and supports the utility of this approach in identifying in vivo targets.

Example 4

RNA Selection to Identify In Vivo FMRP mRNA Targets

Despite the recognition that FMRP is an RNA binding protein (Adinolfi et al. (1999) *RNA* 5:1248-1258; Ashley et al. (1993) *Science* 262:563-566; Brown et al. (1998) *J. Biol. Chem.* 273:15521-15527; Siomi et al. (1993b) *Cell* 74:291-298; Verheij et al. (1995) *Hum. Mol. Genet.* 4:895-901), the inability to identify in vivo RNAs upon which FMRP acts has left a critical gap in the understanding of how its absence leads to mental retardation.

This problem has been approached by combining in vitro RNA selection methods together with biologic studies. Guidance related to RNA selection methods can be found in Ellington and Szostak (1990) *Nature* 346:818-822; Tuerk and Gold (1990) *Science* 249:505-510; Singh et al. (1995) *Science* 268:1173-1176; Wang et al. (1997) *J. Biol. Chem.* 272: 22227-22235); Bartel et al. (1991) *Cell* 67:529-536.

In a few instances, most notably studies on the Hu proteins, a family of RRM-type RNA binding proteins, and Nova, a KH-type RNA binding protein targeted in a neuronal degeneration termed paraneoplastic opsoclonus-myoclonus ataxia (POMA), RNA selection has allowed identification of biologically relevant RNA targets of proteins with previously unknown RNA target specificity (Buckanovich and Darnell (1997) *Mol. Cell Biol.* 17:3194-3201; Jensen et al. (2000a) *Neuron* 25:359-331; Levine et al. (1993) *Mol. Cell Biol.* 13:3494-3504).

RNA selection has now been used to demonstrate that FMRP binds RNA in a specific manner using two different RNA binding domains. Strictly defining the required RNA elements within a G-quartet motif for high affinity FMRP binding has allowed the development of a screen for candidate FMRP RNA targets. This approach has been validated by demonstrating high affinity FMRP binding to 13 candidate mRNAs that harbor stem-loops and fold into G-quartets, including 7 that are highly enriched in FMRP immunoprecipitates from wild-type but not FMRP-null mice, and 6 mRNAs whose polysome distribution is altered in FMRP-null lymphoblastoid cells.

Example 5

The FMRP RGG Box as a Sequence-Specific RNA Binding Element

Although the existence of the disease-associated I304N FMRP mutation has appropriately drawn attention to RNAs that bind to the KH domains, an additional sequence-specific RNA binding domain in the full-length FMRP, the C-terminal RGG box, was unexpectedly found. Previous data has suggested that RGG domains act as non-specific RNA binding domains. In nucleolin, specific RNA binding requires its four RRMs but the presence of an RGG box increases its affinity for its targets 10-fold (Ghisolfi et al. (1992) *J. Biol. Chem.* 267:2955-2959). It has been proposed, based on the secondary structure of the RGG box, that it unstacks adjacent nucleotide bases and unfolds RNA secondary structure, thereby allowing sequence-specific RNA binding domains to access their targets (Ghisolfi et al. (1992a) *J. Biol. Chem.* 267:2955-2959). However, the RGG box of hnRNP U can apparently discriminate between sequences (Kiledjian and Dreyfuss (1992) *EMBO J.* 11:2655-2664). The current results demonstrate that RGG domains are capable of specific RNA target recognition.

Recognition of RNA by the FMRP RGG box appears to have both a structural component—binding to a G-quartet presented in the context of a stem—and a sequence-specific component, since mutagenesis of sc1 nucleotides not involved in either the G-quartet or in the stem are able to markedly reduce FMRP binding (FIG. 3). Specifically, 5 different mutations outside of the GG repeats were able to significantly abrogate binding including a single base change from an A to a C in loop 2, deletion of a nucleotide from each of loops 2 and 3, and a GU to UA change in loop 2. In addition, changing the AA of loop 1 to CC decreased binding to an undetectable level, although we cannot rule out that the presence of this pair of Cs may have disrupted the G-quartet by competing with Hoogsteen base pairing between the conserved Gs. Moreover, the consensus of the RNA selection itself suggests sequence specificity in the loops; for example, a U or an A almost always precedes the GG pairs.

The simplest interpretation of this data is that FMRP has sequence preference for the loops surrounding the G-quartet element. Such complex sequence-specific binding has previously been detected with arginines in the arginine-rich motifs (ARMs) of HIV Rev and Tat, and in Tat one arginine is capable of specifically recognizing a U-A-U base triple (Tao and Frankel (1997) *Biochemistry* 36:3491-3495), illustrating that arginines are capable of complex and sequence-specific interactions with RNA targets.

G-quartet elements have been found in vivo in a number of forms. They can be intramolecular structures, although they have most commonly been reported as bimolecular or tetramolecular structures. It is likely that the structure of the sc1 RNA is an intramolecular G-quartet as opposed to a two- or four-stranded interaction. On native gels, only a single sc1 RNA species is present, and it comigrates with a control 96mer that does not form a G-quartet structure (sc11, data not shown). A band of the expected size of a dimer or tetramer has not been observed. Moreover, the rapid rate at which these form in very dilute RNA solutions (within 10 minutes after 75° C. denaturation at 1.8 nM RNA) as well as selection of these structures out of random pools in which intermolecular interactions are unlikely to occur suggests that it is an intramolecular G-quartet structure that forms.

G-quartet elements serve as physiologic targets of several nucleotide binding proteins. They were first described in protozoan telomeric DNA (Williamson et al. (1989) *Cell* 59:871-880), and were subsequently described as targets of several telomeric DNA binding proteins, including yeast protein RAP1 and the beta subunit of Oxytricha telomere binding protein (Giraldo and Rhodes (1994) *Embo J.* 13:2411-2420; Williamson (1994) *Annu. Rev. Biophys. Biomol. Struct.* 23:703-30). More recently, BLM and WRN (helicases mutated in Bloom's and Werner's syndromes, respectively) have been found to bind DNA G-quartets thought to be involved in genetic recombination (Fry and Loeb (1999) *J. Biol. Chem.* 274:12797-12802; Sun, et al. (1998) *J. Biol. Chem.* 273:27587-27592) and nucleolin and hnRNP D form a complex, LR1, which binds G-quartets involved in IgG heavy chain class switch recombination (Dempsey et al. (1999) *J. Biol. Chem.* 274:1066-1071). See also Oliver et al. (2000) *J. Mol. Biol.* 301:575-584.

Example 6

FMRP KH2 Binding to Distinct RNA Targets

It has now been demonstrated that FMRP acts to bind RNA in a sequence-specific manner through its KH2 domain. Although it has been reported that FMRP KH2 is an atypical KH domain, harboring a large probably unstructured loop sequence (exons 11-12; (Eichler et al. (1994) *Hum. Mol. Genet.* 3:684-685; Lewis et al. (1999) *Structure* 7:191-203) that may not fold properly (Adinolfi et al. (1999) *RNA* 5:1248-1258), the present data suggests that FMRP KH2, like a number of other KH domains analyzed (Berglund et al. (1998) *RNA* 4:998-1006; Buckanovich and Darnell (1997) *Mol. Cell Biol.* l7:3194-3201; Jensen et al. (2000a) *Neuron* 25:359-331; Lewis et al. (1999) *Structure* 7:191-203; Thisted et al. (2001) *J. Biol. Chem.* 276:17484-17496; Yang et al. (1998) *Proc. Natl. Acad. Sci.* 95:13254-13259), is able to function as a high affinity sequence-specific RNA binding domain.

RNA clones sc10 and sc11 bound FMRP KH2 in a manner that was abrogated by the I304N mutation. In contrast to FMRP RGG binding to sc1, binding to sc10 and sc11 was lost in later rounds of RNA selection, suggesting lower affinity interactions by KH2 than by the RGG box in the full-length protein. In addition, filter binding assays demonstrate that FMRP binds sc11 with an affinity of 31 nM versus about 10 nM for sc1, and the isolated KH1 and KH2 domains bound with even lower affinity (Kd~50-100 nM). It is likely that in addition to KH2, KH1 or other RNA-binding domains of FMRP contribute to the affinity of full-length FMRP for sc11. However, since the I304N KH2 point mutation reduces sc11 binding by at least 100-fold, one can conclude that KH2 is necessary but perhaps not sufficient for the highest affinity sc11 binding.

While not limiting the present invention to any particular mechanism, this data suggests that FMRP functions such that a hierarchy of RNA binding domains within the fill-length protein are capable of binding independent RNA sequences. At the same time, these domains may work together to allow FMRP to recognize RNAs harboring more than one RNA target element.

These observations are relevant to consider in the context of the Fragile-X mental retardation syndrome. The development and morphology of the central nervous system appears to be largely intact in these patients, with the primary abnormalities found to be subtle defects in dendritic spine morphology. Moreover, one severely affected patient harbors the I304N mutation within KH2. Solution of the Nova KH3-RNA crystal structure revealed that the KH domain binds RNA in a sequence-specific manner by folding the protein backbone to allow it to act as a scaffold that binds single-stranded RNA in pseudo-Watson-Crick manner (Lewis et al. (1999) *Structure* 7:191-203). This structure revealed that the I304N mutation is located precisely at a position within the KH domain to disrupt sequence-specific RNA binding. While estimates have suggested that 1-4% of total brain mRNAs may be present in FMRP-containing RNP complexes, it seems likely that only a subset of these RNAs may be affected in the development of phenotype in the fragile-X syndrome. The current data presented here suggest that such RNAs could be a subset of transcripts harboring both high affinity sc1-like G-quartet elements and lower affinity sc11-like sequence-specific elements. Alternatively, KH2 recognition sequences might be obscured by the G-quartet secondary structure, in which case the RGG box might function to allow access to these secondary sites, or the two RNA targets could be present in trans- in entirely different RNAs which bind FMRP simultaneously.

Example 7

Identification of FMRP mRNA Targets

RNA selection has been performed in order to identify in vivo RNA targets for FMRP. Guidance regarding the use of RNA selection can be found in Buckanovich and Darnell (1997) *Mol. Cell Biol.* 17:3194-3201; Jensen et al. (2000a) *Neuron* 25:359-331; Lewis et al. (1999) *Structure* 7:191-203.

A detailed analysis of FMRP binding to the sc1 RNA selection target was undertaken in order to develop a stringent screen for candidate FMRP RNA targets. This analysis identified FMRP binding sites in a number of mRNAs, using the RNABob algorithm to search the UniGene database, and to search candidate RNAs identified through co-immunoprecipitation and gene chip analysis or through their altered polysomal distribution in fragile X patient cells.

Example 8

FMRP Target RNAs Encode Proteins Involved in Dendritic Development and Synaptic Function Remarkably, almost all of the 13 mRNAs identified by this strategy (Table 1) have biologic functions of relevance to the fragile-X syndrome. As a group, the RNAs identified encode proteins with roles in maintaining proper synaptic function, mediating neuronal development, or in craniofacial development.

Six mRNAs harboring FMRP target elements are associated with synaptic function. The FMRP binding site characterized in human munc13 and conserved in rat isoform munc13-2 is intriguing because of the role the munc family plays in the regulation of synaptic transmission. The munc13 family is brain-specific, although a splice variant of 13-2 is found at high levels in testes and lung as well, munc 13-2 is present in the rostral brain regions including the cerebral cortex and CA regions of the hippocampus. The munc proteins have been shown to have essential functions in synaptic vesicle priming in the active zone of the synapse. NAP-22 is a $Ca^{+2}$-dependent calmodulin binding protein present in axon terminals and dendritic spines that localizes to the membrane raft domain. It is likely to play an important role in the maturation or maintenance of synapses through its role in regulating membrane dynamics. V1a is a G-protein coupled arginine vasopressin receptor with 7 transmembrane domains. Vasopressin causes a long-lasting facilitation of glutamate-mediated excitation in the septum-hippocampus complex and is thought to facilitate learning and memory. In addition, the V1a receptor is strongly implicated in the regulation of social behaviors and aggression. Kv3.1 is a subunit of a tetrameric voltage-gated $K^+$ channel of the Drosophila Shaw-like subfamily. These channels are important in facilitating sustained or repetitive high frequency firing of the GABAergic interneurons of the neocortex and hippocampus. GEF belongs to a family of mammalian Sec7-like proteins that function as guanine-nucleotide exchange factors, signaling through inositol 1,4,5 triphosphate receptors and PI3-kinase, and are involved in vesicle transport and other activities in neurons (Jackson and Casanova (2000) *Trends Cell Biol.* 10:60-67). Rab6-binding protein was identified by two-hybrid screen of mouse brain with rab6. rab6 is a Golgi localized GTPase that has been shown to play an important role in intracellular vesicle trafficking. Recently rab6 has been shown to be present on a satellite secretory pathway in neuronal dendritic spines. The processing and transport of locally translated integral membrane and secretory proteins is likely to be an important mechanism underlying the dendritic spine changes that mediate long-term synapse-specific modifications.

Three targets encode proteins involved in neuritic extension and neuronal development. An FMRP-binding site in the 5'UTR of the full-length transcript for the microtubule-associated protein, MAP1B has now been identified. MAP1B is a phosphoprotein that is very highly expressed in developing neurons, and appears to play an important role in the extension of axons and dendrites by regulating microtubule stability and organization. Semaphorin 3F is a secreted neuronal protein that has inhibitory and stimulatory effects on growth cones and is essential for the pathfinding of axons. ID3 is an inhibitor of differentiation protein that binds to basic helix-loop-helix transcription factors to form an inactive dimer, and it is expressed in the proliferative zone of the hippocampus that gives rise to granule cells and dentate precursor cells.

Several other candidates are also of interest with respect to fragile-X mental retardation. MINT is a double-stranded DNA binding protein that is expressed at high levels in testes and at lower levels in brain and calvarial osteoblasts. In the latter cell type it binds the osteocalcin promoter and its transcriptional activity is regulated by specific protein-protein interactions with the homeodomain transcriptional repressor msx2, which exerts tissue-specific effects during craniofacial and neural development. Srm kinase is a novel nonreceptor tyrosine kinase that has two transcripts on Northern blot, a 2.6 kb transcript expressed ubiquitously and a 2.0 kb transcript specific for the brain and testes. Little is known about the function of the protein encoded by the EHOC-1 gene. It was cloned as a candidate gene for myoclonus epilepsy and has multiple potential transmembrane domains and partial homologies to sodium channel proteins.

Example 9

Biological Role of Targets Identified by RNA Selection Studies

The finding that many of the RNA targets identified are involved in either synaptic function or dendritic growth fits extremely well with several previous observations regarding the role of FMRP in mental retardation. 1) FMRP is localized to both the axon terminus and the dendrite, where it has been proposed to be involved in translational control, mRNA targeting, or both (Feng et al. (1997) *Mol. Cell* 1:109-118; Jin and Warren (2000) *Hum. Mol. Genet.* 9:901-908). 2) dendritic spine abnormalities are seen in pathologic specimens of brain studied from FMR patients and FMR1-null mice; 3) synaptic plasticity is believed be responsible for important aspects of learning and memory. A growing of literature suggests that activity-dependent local translation may be important in synaptic plasticity. A plausible model is that FMRP binds specific RNA elements, either regulating translation of RNAs important for synaptic function, or targeting of certain mRNAs to the dendrite, where they await signaling that would allow their translation. The ability to functionally tie together the fragile X syndrome, the FMR protein, and the set of FMR RNA targets makes a compelling argument that the failure of FMRP to regulate these mRNAs play a key role in the pathogenesis of the fragile X mental retardation syndrome.

Example 10

Experimental Procedures

Expression and Purification of FMRP Fusion Proteins

PCR amplification of a human fetal cDNA library with primers (5' end: 5'-GAATTCGGAGCTGGTGGTG-GAAGTG-3'; 3' end: 5'-CGGCCGGTTGCTGACCATC-CAC-3') was used to clone the iso7 form of FMRP (Sittler et al. (1996) *Hum. Mol. Genet.* 5:95-102). Iso7 is an alternatively spliced form of FMRP lacking exon 12 but including all the coding sequence from exons 15 and 17. It is the most abundant human form of the protein (Verkerk et al. (1993) *Hum. Mol. Genet.* 2:399-404). Cloning into the EcoRI and EagI (XmaIII) sites of pet21b Novagen, Madison, Wis.) yielded an N-terminally T7 tagged and C-terminally histidine tagged FMRP fusion protein. The construct was extensively sequenced to confirm the correct sequence. Production of protein in IPTG-induced BL21 (DE3) according to manufacturer's instructions (Novagen, Madison, Wis.) reproducibly yielded fusion proteins of 50 kDa or less. These may represent partial translation products or may be due to proteolytic cleavage. To avoid this problem, the pMelBac system (InVitrogen, San Diego, Calif.) was used to express secreted FMRP as a C-terminally His-tagged protein using the honeybee mellitin (HBM) signal sequence that is cleaved by the insect cell during secretion. Histidine tagged, but no longer T7-tagged, FMR1 was cut out of the pet21b clone by partial digestion with BamHI and B1pI. pMelBacB was digested with BamHI and KpnI. Following ligation of the BamHI sites, Klenow fill-in and blunt end ligation of the remaining ends were accomplished by standard protocols. The resulting construct was resequenced and used for production of FMRP-expressing baculoviral stocks from Sf9 cells according to the manufacturer's instructions (InVitrogen).

KH1 and KH2 domain isoleucine to asparagine mutations were introduced into pMelBacB FMR1 by PCR. For KH2 the ATT encoding I304 was changed to AAT, and the analogous mutation made in the KH1 domain, singly and in combination with the KH2 domain mutation.

Individual domains of FMRP were cloned by PCR amplification using pMelBacBFMR1 as a template and ligated into pET21b to produce N-terminally T7-tagged and C-terminally histidine tagged fusion proteins from BL21(DE3) bacteria. The C-terminal deletions were made in the same way using the following primer pairs for PCR. Cterm1: N1+C1, Cterm2: N8+C2, Cterm3: N2+C1, Cterm4: N3+C1, Cterm5: N4+C1, Cterm6: N1+C4, Cterm7: N1+C3, Cterm8: N5+C1, Cterm9: N6+C1, Cterm10: N7+C1. Primer sequences are listed 5' to 3': N1: cggaattcgaaggaagtagaccagttgcg N2: cgggatccgattgat-gagcagttgcgacagattgg N3: cgggatccgaaggaaaaaagctatgtgac N4: cgggatccgagaaatagggggcacggcagac N5: cggaattcgg-gatatacttcaggaactaattctgaagc N6: cggaattcggaatctgaccaca-gagacg N7: cggaattcgcgcagaggagacggacggcgg N8: cggaattc-gacagataatcgtccacg C1: ccgctcgagtcgggagtgatcgtcgttttcc C2: atagtttagcggccgccggttgctgaccatccac C3: ggcctcgaggctctc-cctctcttcctctgttgg C4: atagtttagcggccgcgctaaggtctactacctcg.

Baculoviral fusion proteins were expressed by infection of High Five cells in Excell-405 media (JRH Biosciences, Lenexa, Kans.) containing 2% fetal calf serum (BioWhittaker) for 3 days followed by clarification and dialysis of the media against 2 changes of dialysis buffer (20 mM HEPES, pH 8.0, 600 mM NaCl) at 4° C. Following dialysis proteins were loaded on a 2 ml Chelating Fast Flow Sepharose column (Amersham Pharmacia Biotech, Uppsala, Sweden) prepared according to the pET system manual (Novagen, 4th edition) and equilibrated with IMAC-0 (20 mM HEPES, pH 8.4, 1M KCl). The column was washed sequentially with 20 ml IMAC-0 and 20 ml IDAC-30 (IMAC-0 plus 30 mM imidazole) and FMRP eluted with 200 mM imidazole. FMRP-containing fractions were pooled and dialyzed overnight against PBS (pH 7.4)+5 mM $MgCl_2$. Following dialysis protein was loaded on a 1 ml column of polyguanylic acid immobilized on polyacrylhydrazido-agarose (Sigma Chemical Co., St. Louis, Mo., riboG), pre-equilibrated with riboG binding buffer (10 mM Tris-HCl, pH 7.4, 2.5 mM $MgCl_2$, 150 mM NaCl). The column was washed with 8 ml ribo-G binding buffer containing 250 mM NaCl and protein eluted with binding buffer containing 1M NaCl. Fractions containing FMP were pooled, examined for purity by electrophoresis on 10% SDS-PAGE gels, transferred to nitrocellulose and protein visualized by colloidal gold staining (BioRad) or amido black 10B (Sigma) staining. Proteins were stored in elution buffer and dialyzed just before use into the appropriate buffer.

Bacterial fusion proteins were expressed according to the pET system manual (Novagen) and purified as above except using the purification protocol listed in the manual. Ribo-homopolymer purification was only used for the C-terminus.

In vitro RNA Selection

RNA selection was carried out as described (Buckanovich and Darnell (1997) *Mol. Cell Biol.* 17:3194-3201) with the following exceptions. The buffer used for the application of RNA to the FMRP column was selection binding buffer (SBB, 200 mM KOAc, 10 mM TrisOAc, pH 7.7, 5 mM MgOAc) The column was washed with 10-20 column volumes of SBB before protein elution with SBB+200 mM imidazole. RNA was extracted with acid-phenol at 55° C. for 15 minutes, extracted with chloroform:isoamyl:alcohol (49:1) and ethanol precipitated with glycogen. RNA was reverse transcribed with Superscript (Gibco BRL, Life Technologies) and PCR amplified with selection primers (Buckanovich and Darnell (1997) *Mol. Cell Biol.* 17:3194-3201). The PCR product was passed over an S-400 (Amersham Pharmacia Biotech, Inc.) column and used as a template for in vitro transcription and further rounds of selection. Selection of pools continued as long as the Kd of FMRP for the pool of RNAs increased at each round by filter binding assay. 24 clones from round 7, 15 clones from round 8 and 24 clones from round nine were sequenced following TA cloning (InVitrogen) of the PCk reaction.

Nitrocellulose Filter Binding Assays 100-200 nmoles of internally labeled RNA (preheated to 75° C. and bench cooled 5 minutes) was incubated with the indicated concentrations of protein in a total volume of 50 μL in SBB for 10 minutes at room temp. Binding solutions were passed through MF-membrane filters (0.45 HA, Millipore) and washed with 5 ml SBB. Filters were air dried and counted in 5 ml ReadiSafe scintillant. Data were plotted as percentage of total RNA bound versus log of the protein concentration and Kd values determined using Kaleidograph software (Synergy Software). Where indicated LiOAc was substituted for KOAc in the SBB.

Electrophoretic Mobility Shift Assay

Native gel electrophoresis was performed at 4° C. in 0.5× TBE in gels of 6% polyacrylamide (acrylamide:bis ratio 39:1). RNA was diluted to 5000 cpm/µl in RNA dilution buffer (100 mM KOAc, 50 mM TrisOAc, pH 7.7, 5 mM MgOAc), heated to 60° C. for 5 min and an equal volume of 15% Ficoll added. 5 µl RNA was added to each sample in a total volume of 20 µl in gel shift buffer (50 mM KOAc, 50 mM TrisOAc, pH7.7, 10 mM DTT, 5 mM Mg(OAc)$_2$, 30 µg/ml tRNA). Final FMRP or Nova concentration was 100 nm. After addition of RNA samples were incubated at 4° C. for 20 min. Gels (BioRad minigels) were prerun at 100V for 20 min and voltage increased to 200V at the time of sample loading. Gels were run 20 min and transferred to Whatman paper for exposure to autoradiographic film (Kodak MR). Where indicated monoclonal antibodies, 1 µl, (anti-FMRP is Mab2i6O, Chemicon, anti-T7 from Novagen) were mixed with the proteins before the addition of RNA. The control rRNA is a 230 bp piece of domain 4 from mouse).

Boundary Mapping

In vitro transcribed sc1 RNA (60 pmol) was 3' end labeled with T4 RNA ligase (New England Biolabs) and $^{32}$P-pCp (Amersham). Sc1 RNA (40 pmol) was 5' end labeled with T4 polynucleotide kinase (New England Biolabs) and γ-$^{32}$P-ATP following dephosphorylation with calf intestinal alkaline phosphatase. Following gel purification labeled RNA was digested with RNAse T1 (Gibco BRL, 1180 units/µl) by preheating 2 µl RNA with 6 µl 1.25×T1 buffer (8.75 M urea, 625 mM Na-Citrate, pH 5, 1.25 mM ETDA) at 50° C. for 2 minutes. 2 µl T1 was added for 4 min at 50° C. and stopped by addition of 6 µl loading buffer (USB). RNAs were subject to mild alkaline hydrolysis by incubating 10 µl RNA in 50 mM Na carbonate, pH9, at 95° C. for 8 minutes. Hydrolyzed RNA was ethanol precipitated with glycogen, 75% ethanol washed and resuspended in 20 µl DEPC water for incubation with FMRP. 5 µl aliquots of hydrolyzed RNA were used in standard filter binding assays with and without 100 nM FMRP. Following SBB wash, filters were eluted with 200 µl 7 M urea, 400 µl acid phenol and 130 µl chloroform in a microcentrifuge tube, shaling at room temperature 45 min. 130 µl water was added, vortexed and microcentrifuged 5 min. Eluted RNA was ethanol precipitated from the supernatant. RNA samples were run on sequencing size 8% urea-PAGE gels with 0.2 mM spacers, dried and bands visualized by autoradiography.

Point Mutations in sc1

Mutations were introduced into sc1 RNA by synthesis of a 3' oligo encoding the nucleotide change and use of this with an appropriate 5' oligo and sc1 as a template in PCR reactions. These PCR products were checked on a 2% agarose gel for amplification, passed over a G-25 column (Amersham Pharmacia Biotech) and used as templates for in vitro transcription.

RNAse T1 Digestion

5' end-labeled sc1 or sc11 RNA was digested with 0.2 units RNAse T1 in 100 µl aliquots of 150 mM KCl or LiCl, 100 mM Tris-HCl, pH 7 for 5 min at 37° C. or the time indicated. For the time course, 10 µl aliquots were removed at the indicated times and stopped with 6 µl formamide loading buffer. Sequencing size gels were run as above.

B. Identification of mRNAS Bound by FMRP by Immunoprecipitation and Microarray Analysis Example 11

Figure 5:
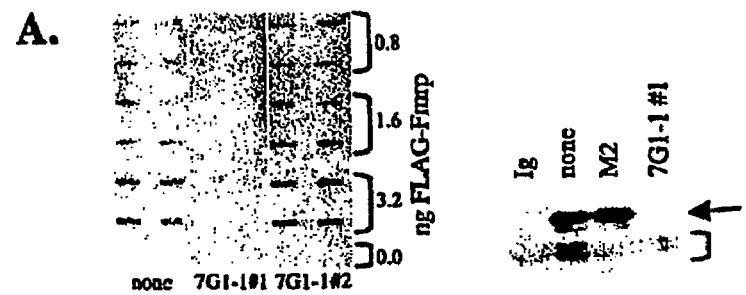
FIG. 5 shows results of immunoprecipitation of the FMRP-mRNP complex. (A) Left: Competitive Western blot analyses were performed with purified FLAG-FMRP and probed with 7G1-1 antibody mixed with the indicated peptide competitors at 1000× molar excess. The labels mean the following: none, no peptide; 7G1-1 #1, 354KHLDTKENTHFSQPN368; and 7G1-1 #2, 367PNSTKVQRVLVSSIV382. Right: Peptide 7G1-1 #1 blocks immunoprecipitation of FMRP. Lysates prepared from the FLAG-FMRP-expressing L-M cells (Ceman et al. (1999) *Mol. Cell. Biol.* 19: 7925-7932) were immunoprecipitated with 7G1 that was untreated (none), preincubated with the irrelevant FLAG M2 peptide (M2), or preincubated with the peptide 7G1-1 #1 (7G1-1 #1). Antibody matrix alone is shown in the lane marked Ig. Precipitates were probed with the 1C3 anti-FMRP antibody. FMRP is indicated by the arrow; antibody chains are indicated by the bracket. Bottom: Partial protein alignment of human (h) and murine (m) Fmr and Fxr proteins. MAb 7G1-1 recognized the boxed amino acids 354-368 of mFMRP, in a region with no homology to the Fxr paralogs. (B) Whole brain lysates were prepared from wt or Fmr1 KO mice, immunoprecipitated with the mAb 7G1-1, and probed with the 1C3 anti-FMRP antibody. The labels mean the following: lysate, input; flow thru, unbound; and IP, immunoprecipitated material. (a) indicates FMRP isoforms, and (d) indicates antibody chains. (C) Paralogs, FXR2P and FXR1P, coprecipitate with FMRP. The left panel shows probing with (a) anti-FMRP antibody (1C3), and (b) anti-FXR2P antibody (A42). A separate aliquot was probed with anti-Fxr-1 antiserum (right panel, c). (D) FMRP associates with poly(A)+RNA in mouse brain. Immunoprecipitations were performed from wt and KO brain lysates, RNA was extracted, and first strand cDNA was generated and visualized by autoradiography.
Figure 5:
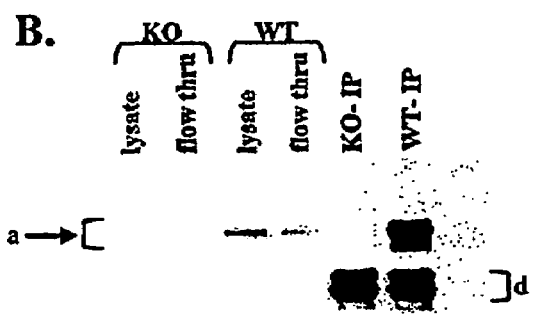
Figure 5:
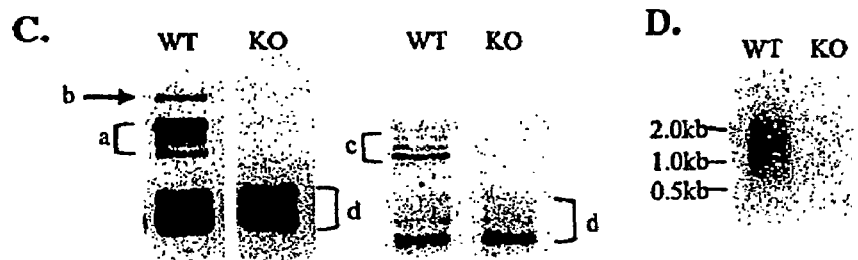

Strategy to Isolate and Identify mRNAs Associated with FMRP-Containing mRNP Particles To identify mRNAs associated with FMRP in vivo, a strategy was devised to specifically immunoprecipitate FMRP-containing mRNP particles and to identify the co-purified mRNAs by probing microarrays. See Tenenbaum et al. (2000) *Proc. Natl. Acad. Sci. USA* 97:14085-14090. For murine FMRP, a monoclonal antibody (mAb 7G1-1) was developed by immunizing the FMR1 knockout (KO) mice with mouse FMRP (Brown et al. (1998) *J. Biol. Chem.* 273: 15521-15527). The epitope recognized by mAb 7G1-1 was mapped to a region of nonhomology with the Fxr1 and Fxr2 proteins (FIG. 5A). Immunoprecipitations from whole brain lysates of wildtype (wt) and KO sibling mice (congenic on the C57B1/6J strain) revealed that the antibody efficiently immunoprecipitates at least three of the predominant FMRP isoforms (FIG. 5B, a). Although the antibody does not immunoprecipitate the Fxr proteins from KO brains (FIG. 5C, lanes KO), both Fxr1p and Fxr2p were found associated with FMRP in wt mouse brain (FIG. 5C, lanes wt, b, and c), demonstrating the immunoprecipitation of the mRNP complex. Nucleic acid extraction of the immunoprecipitant and oligo dT-primed reverse-transcription showed the presence of poly(A)$^+$ RNA. Very little background RNA was found in the control immunoprecipitations from the KO brain lysates (FIG. 5D).

Example 12

Microarray Analysis of the Resident mRNAs in the FMRP-mRNP Complex

En masse identification of the mRNAs co-immunoprecipitated with the FMRP mRNP complex was achieved using the Affymetrix Murine Genome U74 (MG-U74) and Murine 19K (Mu19K) oligonucleotide microarrays. These arrays allowed the interrogation of 25,181 RNAs from the UniGene database and 19,021 messages from the TIGR database, respectively. For independent array screens, fresh lysates from pooled wt and from pooled KO brains (2 each) were prepared and 20% of the total volume of each lysate was used to isolate total RNA as input RNA. The remainder of the brain lysates was subjected to 7G1-1 mAb immunoprecipitation (IP) followed by RNA extraction to isolate the IP RNA. wt-IP and KO-IP RNA samples were used to generate cRNA that was hybridized, in parallel with cRNA generated from input RNA, onto identical MG-U74 arrays. Microarrays probed with input RNA exhibited bright fluorescence, consistent with the complex gene expression pattern of the murine brain. Less than 0.05% of the RNAs were substantially changed when comparing wt versus KO whole brain lysates (results elsewhere), indicating FMRP deficiency does not result in widespread mRNA changes at steady state. Consistent with earlier studies suggesting FMRP associates with only a subset of mRNAs (Ashley et al. (1993) *Science* 262:563-566), the wt-IP microarrays showed substantial intensity loss for most of the genes found to be expressed in the input lysate. The KO-IP microarrays exhibited further intensity loss when compared to the wt-IP. Although detectable signals were evident on the KO-IP arrays, these were presumably due to background interactions with the antibody matrix, independent of FMRP.

Figure 6:
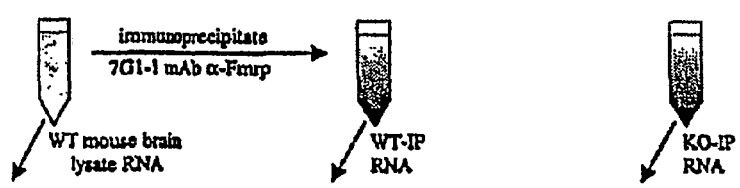
FIG. 6 illustrates analysis of the RNAs coimmunoprecipitated with the FMRP-mRNP. (A) The MG-U74 gene chips were hybridized with cRNA generated from total RNA from wt brain input lysate (input, left panel), from RNA coimmunoprecipitated with FMRP from wt mouse brain (wt-IP, center panel), or from RNA immunoprecipitated from Fmr-1 KO mouse brain (KO-IP, right panel). (B) Venn diagram of the RNAs associated with the FMRP-mRNP. The square depicts the genes available on the MG-U74 chips. The white ellipse represents the genes detected in the wt brain lysate input. The large circle indicates the 2,902 genes enriched in the wt-IP versus KO-IP. The small circle shows the 527 genes enriched in the wt-IP versus the input. The intersection of these circles indicates those genes enriched in the wt-IP in both analyses.
Figure 6:
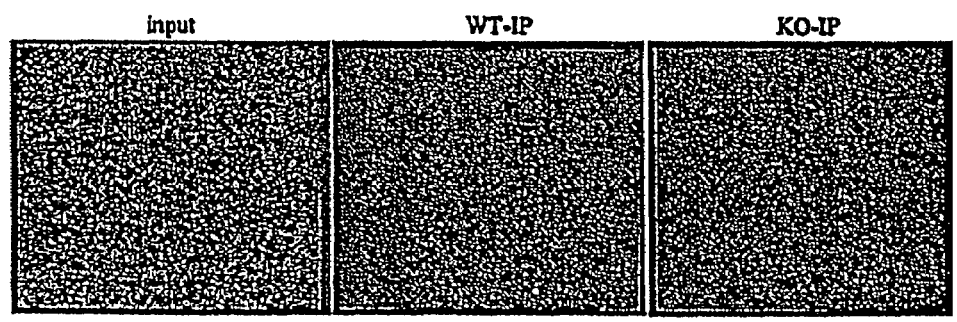
Figure 6:
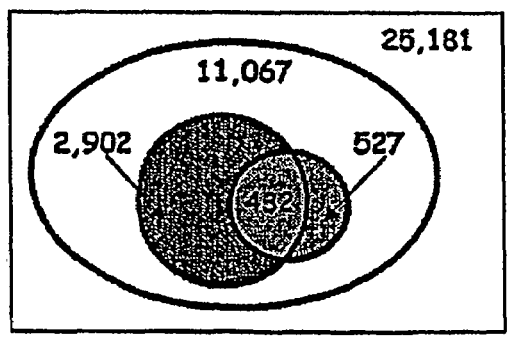

Of the 25,181 total genes available on the MG-U74 microarray, 11,067 genes (~44%) were present in the total wt brain lysate. The analysis of the co-immunoprecipitated mRNA was carried out in two parts; first the wt-IP mRNA profile was analyzed using the KO-IP mRNA profile as the baseline, and second, wt-IP mRNA profile was compared against the total wt input RNA profile. The former analysis presumably identifies FMRP-independent mRNAs associated with the antibody-matrix, while the latter analysis identifies those mRNAs scored as present in the wt-IP relative to the wt input, discarding those mRNAs whose high abundance in the input lysate may be responsible for their presence in the IP sample. While discarding genes in either of these approaches may remove bona fide FMRP-associated messages, it results in a relatively stringent selection and should minimize false positives. As displayed in the Venn diagram FIG. 6B), 2,902 mRNAs (26% of expressed messages) were at least 4-fold enriched in the wt-IP mRNAs when compared to the KO-IP mRNAs. However, many of these enriched mRNAs are also found at high abundance in the input lysate such that, of the 11,067 expressed genes in the total input brain lysate, only 527 mRNAs (5% of expressed messages) showed a 4-fold or greater enrichment over the input lysate by immunoprecipitation (FIG. 6B). Combining these two results showed that 15% of the 2,902 genes identified in the first analysis and 82% of the 527 genes identified in the second analysis were identical and met both criteria for enrichment in the wt-IP (FIG. 6B). The intersection conservatively represents 432 genes, or 3.9% of the 11,067 expressed RNAs. This number is remarkably consistent with an earlier and much more crude estimate, suggesting that ~4% of human fetal brain messages associated with FMRP in vitro (Ashley et al. (1993) Science 262:563-566).

The top 80 mRNAs enriched in the FMRP-mRNP are shown in Table 2 (below). The genes were sorted in descending order by the 'fold change' in the wt-IP versus KOIP (baseline) comparison, and then sorted again in descending order by the 'fold change' in the wt-IP versus input (baseline) comparison. The final rank of each probe selects the sum of these two fold change values: [wt-IP vs. KO-IP]+[wt-IP vs. input]. The largest message enrichment in the wt-IP when compared with the KO-IP was 77-fold for a Sec7-related transcript KIAA0763, identified by homology as the guanine nucleotide exchange factor. The transcript for SAPAP4, encoding the PSD95-associated protein 4, had the highest wt-IP enrichment over wt input lysate, which was approximately 34-fold. The highest average difference changes of the wt-IP relative to the message prevalence in the lysate was approximately 18,000 and 14,000 for the transcript similar to Peroxidasin and the Septin 3 GTPase, respectively. All transcripts ranked in the top 20 had average difference changes (versus input) in excess of 1,000.

An independent immunoprecipitation experiment was performed and analyzed using a different version of the Affymetrix murine gene chips, the Mu19K expression array. Using the same criteria as in the MG-U74 experiment, genes showing a 4-fold or greater enrichment during the immunoprecipitation were identified. When the two independent experiments were compared, 36 of the top 80 RNAs described in Table 2 (below) were not available on the Mu19K chips, and therefore were not tested by the Mu19K data (Table 2, N/A). However, the Mu19K array data confirmed the FMRP-mRNP enrichment for 28 of the 44 genes tested (64%) (Table 2). It should be noted however that a number of genes were represented on both array types but with different sequences in the oligonucleotides, potentially confounding reproduction of the MG-U74 data.

TABLE 2

Messenger RNAs Associated with the Fmrp-mRNP in Mouse Brain

| | | MG-U74 | | Mu 19K |
|---|---|---|---|---|
| Rank | Homology (MG-U74 Probe Set) | wtIP/KOIP Fold Chg. | wtIP/Input Fold Chg. | wtIP/Input Fold Chg. |
| 1 | Sec7-rel. GEF sim. to KIAA0763 (112719_at) | 77 | 14.5 | 6.8 |
| 2 | Tyrosine Kin.,, AATYK (100994_at) | 52.4 | 12.7 | N/Aa |
| 3 | iGluR, kainate-R 5_2, Grik5 (104409_at) | 41.8 | 21.4 | N/A |
| 4 | Brain Angiogen. Inh., BAI2 (106947_at) | 43.6 | 19.3 | 4.4 |
| 5 | PSD-95 assoc.SAPAP4, KIAA0964 (104136_at) | 28.4 | 33.8 | 6.7 |
| 6 | Zn. finger Mtsh-1 (106265_at) | 50.4 | 11.6 | 7.5 |
| 7 | murine Unc13-like prot. (110722_at) | 50.1 | 11.1 | N/A |
| 8 | Arf GTPase acivator, GIT1 (97339_at) | 22.5 | 33.7 | 1.8 |
| 9 | Pumilio 2 (112390_at) | 49.3 | 5.5 | 4.2 |
| 10 | K_channel HCN2, HAC1 (94194_s_at) | 25.1 | 27.8 | N/A |
| 11 | sim. to DAP-1 and SAPAP3 (116746_at) | 46.8 | 5.1 | N/A |
| 12 | GAP-assoc. p190 (96208_at) | 29.7 | 22.1 | 11.9 |
| 13 | KIAA0284 sim. to Septin 3 GTPase (131216_f_at) | 23.5 | 27.1 | N/A |
| 14 | sim. to KIAA0561 (104032_at) | 20.4 | 29.6 | 15.8 |
| 15 | G prot. effector, GRIN1, Z16 (113864_at) | 27.2 | 22.2 | N/A |
| 16 | sim. to PS1-BP, p0071, plakophilin4 (96187_at) | 35.4 | 12.6 | 9.5 |
| 17 | KIAA0918, TOLL-related prot. (107354_at) | 40.5 | 6.3 | N/A |
| 18 | KIAA0602, ribosomal S7 prot. (111873_at) | 37.7 | 7.3 | 9.6 |
| 19 | Zn. finger Friend of GATA1, FOG (97974_at) | 16.9 | 27.7 | 1.9 |
| 20 | sim. to 5_AMP-activ'd kinase (139527_at) | 25.7 | 18.9 | N/A |
| 21 | Inositol 1,4,5 triphos. recept. p400 (94977_at) | 37.3 | 4.7 | 1.9 |
| 22 | Rab6-assoc. GDI (104108_at) | 34.8 | 6.5 | 6.6 |
| 23 | pBR140, Peregrin (114619_at) | 33.6 | 7 | 13.5 |
| 24 | Nuclear P'tse, dsPTP, myotubularin-rel. (111847_at) | 25.8 | 14.7 | 1.2 |
| 25 | DM prot., DMR-D9(96193_at) | 19.5 | 20 | 1 |
| 26 | Celera mRNA hCT8453 (104299_at) | 31.4 | 7.6 | N/A |

TABLE 2-continued

Messenger RNAs Associated with the Fmrp-mRNP in Mouse Brain

|  |  | MG-U74 | | Mu 19K |
| --- | --- | --- | --- | --- |
| Rank | Homology (MG-U74 Probe Set) | wtIP/KOIP Fold Chg. | wtIP/Input Fold Chg. | wtIP/Input Fold Chg. |
| 27 | Steroid recept. Co-activator le (106920_at) | 32.6 | 6.4 | 9.8 |
| 28 | Hsp75-like TNF1R-assoc. prot. (95886_g_at) | 21.8 | 17.1 | 2.9 |
| 29 | sim. to Interleukin-enhancer-BF1 (95596_at) | 19.8 | 17.9 | 1.1 |
| 30 | sim. to Adenylate Cyclase 5&6 (138967_i_at) | 18.1 | 19.3 | N/A |
| 31 | L-type Ca2_chan. B3, Cacnb3 (98483_at) | 31.8 | 5.3 | 2.4 |
| 32 | Celera mRNA hCT12896; KIAA0701 (109149_at) | 30.8 | 5.2 | 8.3 |
| 33 | sim. to MAP1A and MAP1B (116100_f_at) | 29.1 | 6.3 | 4.5 |
| 34 | Testis prot. Kin., Tesk1 (102033_at) | 19.6 | 15.3 | 2 |
| 35 | KIAA0306, Pro.-rich MP-3, PRP3 (96725_at) | 24.6 | 9.9 | 2.8 |
| 36 | Celera hCT14692 sim. to KIAA1246 (131226_at) | 17.3 | 17 | N/A |
| 37 | sim. to KIAA0918 prot. (134810_s_at) | 11.7 | 22.6 | N/A |
| 38 | Celera mRNA hCT7158 (103736_at) | 27.9 | 6.3 | N/A |
| 39 | Circ. Rhythm prot., SCOP, KIAA0606 (109399_at) | 29.5 | 4.6 | 8.7 |
| 40 | Celera mRNA hCT9545(106009_at) | 27.1 | 6.4 | N/A |
| 41 | KIAA1042 prot. (96124_at) | 26.1 | 7.3 | 5.6 |
| 42 | Rho-interact. P116 RIP (94899_at) | 26.7 | 6.6 | 2.7 |
| 43 | Rab3-assoc.GEF, sim. to MADD (105258_at) | 18.9 | 14 | 10.1 |
| 44 | MHC H2-K(114777_i_at) | 28.6 | 4.2 | 2 |
| 45 | Celera mRNA hCT8410 (104105_at) | 21.1 | 10.3 | 14.6 |
| 46 | Na_channel-related prot.(97387_at) | 25.5 | 5.8 | 2.1 |
| 47 | PI 4 kin., p230 (104208_at) | 17.4 | 13.9 | 5.5 |
| 48 | Msx2-BP, Mint (110008_at) | 26.6 | 4.6 | N/A |
| 49 | Spectrin_3, Spnb3 (93618_at) | 21.6 | 9.3 | N/A |
| 50 | Celera mRNA hCT28708(112918_at) | 23.5 | 6.7 | N/A |
| 51 | hCT25324, Ub-lig.-like(109944_at) | 16.7 | 13.5 | 4 |
| 52 | Celera mRNA hCT25324 (92958_at) | 20.6 | 9.4 | 4.3 |
| 53 | Patched-related prot.(104030_at) | 21.5 | 8.4 | N/A |
| 54 | KIAA0633 prot. (108712_at) | 25.3 | 4.6 | N/A |
| 55 | Celera mRNA hCT33144 (108765_at) | 22.5 | 7.2 | 13.7 |
| 56 | NAG-6-O-sulfotrans. (102639_at) | 22.3 | 7.3 | 5.9 |
| 57 | MAPK4, p63 (140436_at) | 22 | 7.6 | N/A |
| 58 | Zn. finger Rantes(103369_at) | 18.5 | 11 | 3.3 |
| 59 | OCAM-GPI precursor; NCAM2 (96518_at) | 15.8 | 13.7 | N/A |
| 60 | 2-Oxoglutarate dehydrog'se (96879_at) | 25 | 4.4 | 12.4 |
| 61 | a-Latroxin receptor (112497_at) | 23.2 | 6.2 | 4.4 |
| 62 | SNF1-related kinase (97429_at) | 18.8 | 10.3 | 4.9 |
| 63 | Celera mRNA hCT19890(103316_at) | 16.2 | 12.9 | N/A |
| 64 | sim. to MKP-1, -L, & -6 dusPTP'tase (133560_at) | 14.1 | 15 | N/A |
| 65 | Celera mRNA hCT33304(102969_at) | 23.1 | 5.9 | N/A |
| 66 | sim. to Myotubularin (104427_at) | 14.2 | 14.6 | 1.6 |
| 67 | Celera mRNA hCT13240(130936_f_at) | 11.9 | 16.9 | N/A |
| 68 | PI 3 kin., reg. subu. P85b, Pik3r2 (102759_at) | 21.6 | 7.1 | 6.9 |
| 69 | Vav-related KIAA1626 (112513_at) | 13.9 | 14.8 | N/A |
| 70 | Casein kin. Ig2 (96284_at) | 24.4 | 4.2 | 5.6 |
| 71 | Zn. finger Png-1; myelin Mytl1 (96496_g_at) | 11.5 | 16.6 | N/A |
| 72 | sim. to Tensin (110429_at) | 23.4 | 4.1 | N/A |
| 73 | sim. to Synaptotagmin-related prot. (93821_at) | 16.4 | 11 | N/A |
| 74 | M-RdgB2 (139194_at) | 20 | 7.3 | N/A |
| 75 | Tyrosine Kin., Ack; Cdc42 (102850_at) | 15.9 | 11.1 | 2.7 |
| 76 | sim. to TMEM1 (104202_at) | 20 | 6.9 | N/A |
| 77 | sim. to Link GEF II (105927_at) | 13.2 | 13.6 | N/A |
| 78 | sim. to Acetylglucosaminyl transf se (103276_at) | 21.1 | 5.4 | N/A |
| 79 | Down syndr.cell adhes. molec., Dscam (116463_at) | 13.2 | 13.3 | N/A |
| 80 | sim. to D. melanogaster Peroxidasin (130534_i_at) | 19.1 | 7.3 | N/A |

Table 2. Probe sets are ranked by the sum of the fold change values [(wt-IP versus KO-IP) + (wt-IP versus Input)] determined by MG-U74 microarray analysis. aN/A denotes Fmrp-mRNP-associated RNAs determined by MG-U74 not represented on the Mu19K chips.

Example 13

Confirmation of the Association Between FMRP-mRNP and the mRNAs Identified by Microarrays To independently demonstrate that the mRNAs identified in Table 2 are associated with the FMRP-mRNP, fresh immunoprecipitations were performed in the presence of an excess of non-specific RNA competitors, either yeast tRNA or heparin. Neither tRNA nor heparin abrogated the specific RNA association with the FMRP-mRNP for a random group of messages from Table 2 (data not shown). The next question asked was whether an RNA ligand that co-purifies with another RNP would be present in the FMRP-mRNP. The U1-70K small nuclear RNP (snRNP) is a splicing complex that specifically binds the U1 snRNA (Query et al. (1989) Cell 57:89-101). This complex was immunoprecipitated from fresh wt and KO lysates using an anti-U1-70K mAb, and in parallel the FMRP-mRNP was immunoprecipitated from the same lysates (not shown). The anti U1-70K antibody efficiently precipitates the U1-70K protein from both wt and KO brain lysates, whereas the anti-FMRP 7G1-1 antibody precipitates FMRP, as expected, only from the wt brain lysate. The RNA recovered from each precipitation was analyzed by RT-PCR. For each gene of interest, the primer pairs were also tested in a RT-PCR reaction with 0.1 µg of total brain RNA (not shown). The U1 snRNA, previously determined to be the U1-70K ligand, was enriched in the U1-70K precipitates from both wt and KO mouse brain. However, this same RNA was not found in substantial amounts in the FMRP precipitate (not shown). In contrast, the eight tested FMRP-associated mRNAs were only found in the FMRP precipitate from wt mouse brain and not in the U1-70K precipitates nor in the control anti-FMRP immunoprecipitation from KO brain (data not shown). In a set of random mRNAs that were not enriched in the FMRP-mRNP microarray studies, including the neuronal mGluR4, Dynamin, and Homer messages, none were detected in either the U1-70K or FMRP complexes (data not shown).

To further confirm the microarray data, quantitative light-cycler RT-PCR analysis was performed using RNAs from wt-IP and wt input. As shown in Table 3 (below), of three tested mRNAs that were not found by microarray analysis to be enriched in the wt-IP, all showed little enrichment upon light-cycler analysis. In contrast, three genes that were found in the microarray analysis to be enriched in the wt-IP, relative to wt input, were also found to be highly enriched in the IP by quantitative RT-PCR. Indeed, the Sec7-related gene, predicted by the microarray analysis to be highly enriched in the wt-IP, showed over a 60-fold enrichment in the wt-IP over the wt input by light-cycler analysis. The above experiments confirm the microarray data and demonstrate that a subset of brain mRNAs is reproducibly associated with the FMRP-mRNP complex from the mammalian brain.

TABLE 3

Verification of Microarray Data Using LightCycler Real-Time PCR

| Genes | Mouse UniGene Cluster | Association with FMRP-mRNP Determined by Microarray Analysis | Scaled Fold Enrichment in wt-IP over wt-INPUT by LightCycler PCR |
|---|---|---|---|
| Similar to microsomal glutathione S-transferase 3 | Mm. 29823 | No | 1.87 |
| Glutamate receptor, ionotropic, AMPA1 | Mm. 4920 | No | 1.83 |
| Synaptotagmin 1 | mM. 5101 | No | 1.02 |
| KIAA0317 protein | Mm. 24446 | Yes | 31.3 |
| TP63 | Mm. 54143 | Yes | 36.8 |
| Sec7-rel. GEF similar to KIAA0763 | Mm. 89798 | Yes | 60.5 |

Example 14

Altered Polyribosomal mRNA Profile in the Absence of FMRP

While the above experiments point to potential RNA ligands of the FMRP-mRNP complex, they do not address any functional attributes of this association. In an independent series of experiments, microarray analysis was again utilized but now to discern any shifts in individual mRNAs, in the presence or absence of FMRP, on a sucrose gradient that fractionates messages by their relative association to ribosomes. Previous studies have shown most FMRP to be in the polyribosome fractions of cell lyates (Eberhart et al. (1996); Feng et al. (1997) Mol. Cell 1:109-118; Khandjian et al. (1996); Tamanini et al. (1996). In fragile X cells, without FMRP, the FXR proteins do not substantially change in their translational profile (Feng et al. (1997) Mol. Cell 1:109-118). Thus, it appears that a similar mRNP may form with just the FXR proteins, although it may be hypothesized that the absence of FMRP in this complex could alter the translational profile of a subset of mRNAs. To test this hypothesis, microarrays were utilized to compare the mRNA profiles associated with high-molecular-weight polyribosomes between normal human cells and cells derived from fragile X syndrome patients. If changes in the translational profile of messages are observed in the absence of FMRP, these mRNAs should, at least partially, correlate to the immunoprecipitation data if it is functionally important.

To reduce any inherent individual variation that is unrelated to FMRP, we performed sucrose gradient fractionation from pooled (5 cell lines each) as well as individual human lymphoblastoid cell lines, derived from either normal males or fragile X full mutation males. Consistent with previous observation (Feng et al. (1997) Mol. Cell 1:109-118), in pooled normal cells, FMRP associates with polyribosomes (not shown). Neither FMR1 message nor FMRP can be detected in any of the fragile X cell lines (data not shown). RNA was purified from total cytoplasmic extract (total mRNA), as well as from the high-molecular-weight polyribosome fractions. cRNA was prepared for hybridization onto microarrays containing more than 35,000 human genes and/or ESTs (Affymetrix Hu35K). Expression profiles of polyribosomal fractions from both individual and pooled fragile X cells were compared with polyribosomal fraction from either individual normal cells or pooled normal cells (baselines). In addition, expression profiles of total mRNA from pooled cells were compared to each other as well.

Overall, of >35,000 genes analyzed, ~11,000 were present, indicating that about one third of the genes represented on the microarray are expressed in the human lymphoblastoid cells. As might be expected, greater variation in gene expression was observed when the samples were derived from individual cell lines, rather than from the pooled cells (data not shown). In fragile X cells, the FMR1 locus is transcriptionally repressed (Sutcliffe et al. (1992) Hum. Mol. Genet. 1:397: 400) and therefore serves as an ideal internal control. On the microarray, the FMR1 mRNA was clearly present in total mRNA from normal cells, but was absent in fragile X cells. In polyribosomal fractions, the FMR1 mRNA was present in normal cells, although at a low level, but again was completely absent in fragile X cells (not shown). Thus this approach correctly identified the one known difference in mRNA expression between the normal and fragile X cells.

Overall, 144 genes from pooled fragile X cells were changed compared to pooled normal cells in the total mRNA, while 282 genes showed consistent changes in the fragile X polyribosome fractions (pooled or individual fragile X cells) compared to the normal polyribosome fraction (pooled or individual normal cells). Of these 426 genes, 31 were found in both data sets. Because the alteration of a message in the total mRNA may influence the amount of that message in the polyribosome fractions, these 31 mRNAs were eliminated from further analysis. The remaining 113 genes that showed differences in total mRNA were not considered further here. Hence, we were left with 251 genes that show equivalent levels of expression in the total mRNA of pooled fragile X and normal cells but displayed consistent evidence of a translational shift between the two cell types (i.e. the proportion of a message on high-molecular-weight polyribosomes) (not shown). These genes were clustered into two groups based on whether they were increased or decreased in the polyribosomes of fragile X cells. Of the 251 genes, 136 were increased and 115 decreased in the polyribosomes of fragile X cells.

To verify these data, quantitative light-cycler RT-PCR was performed. A control gene, X-linked hypoxanthine phosphoribosyl transferase (HPRT), which did not show any change in either polyribosomal fractions or total mRNA on microarray analysis, was also unchanged in the RT-PCR experiments (data not shown). Consistent with microarray data, quantitative RT-PCR showed that the transcript levels of NAP-22 and MKPX decreased in the polyribosomal fractions of fragile X cells while GRP58 increased in these fractions. There was no significant change in total mRNA from any of the three genes. To further confirm the microarray data, the distribution of NAP-22 and MKPX messages in freshly-prepared sucrose gradient, fractions were probed by Northern blot. Both NAP-22 and MKPX were reduced in polyribosomal fractions of fragile X cells, although total cytoplasmic RNA showed no differences between normal and fragile X cells (data not shown). Glyceraldehyde phosphate dehydrogenase (GAPDH), as a control, did not show any difference between normal and fragile X cells throughout the gradient or in total RNA (not shown). These results confirmed a translational shift of a subset of mRNA in the absence of FMRP.

Example 15

Correlation of Immunoprecipitated mRNAs with those Showing a Translational Shift in Fragile X Syndrome Cells To compare the genes associated with FMRP-mRNP in the mouse brain with the human genes exhibiting abnormal polyribosomal shift in the absence of FMRP, HomoloGene database was searched, using the UniGene clusters that represented the mouse genes of interest, and identified UniGene clusters of the human orthologs of these genes. Conversely, using the human UniGene clusters and probe set information provided by the manufacturer (EASI DATABASE v2.41, Affymetrix), the oligonucleotides that represent the murine orthologs of the human genes were also identified. Of the top 80 genes identified in mouse microarray analysis (Table 2), 48 genes are represented on the Human 35K set oligonucleotide microarray. Among these 48 genes, 28 are expressed in the human lymphoblastoid cells and 14 (50%) were differentially associated with polyribosomes in the normal versus fragile X cells. This appears rather significant because the entire polyribosomal mRNA profile of normal vs. fragile X cells, comparing some 11,000 messages, showed only 2% of the messages as changed in the polyribosome fractions. The other 14 genes, whose messages co-immunoprecipitated with FMRP but did not exhibit abnormal polyribosomal shift, may represent mRNAs associated with the Fxr proteins, potentially revealing the speculated partial compensatory functions of the Fxr proteins. The mRNAs that differentially associated with the polyribosomes of fragile X cells and were also found in the FMRP-mRNP particle are shown in Table 4. Approximately half of these were increased (6/14) and half decreased (8/14) in the high-molecular-weight polyribosomes of fragile X cells. Although FMRP has been shown to suppress translation of bound messages in vitro (Li et al. (2001) *Nucleic Acids Res.* 29:2276-2283; Laggerbauer et al. (2001) *Hum. Mol. Genet.* 10:329-38), perhaps accounting for the 6 messages showing increased loading on polyribosomes in the absence of FMRP, the exact effect of FMRP on translation in vivo would appear to be more complex.

TABLE 4

Changed mRNAs in the Fra(X) Polyribosome Fraction that also Co-immunoprecipitate with Mouse Brain Fmrp mRNP

| Gene Name | Presence of Putative Stem/G-quartet Loop Structure | Human UniGene Cluster | Mouse UniGene Cluster | Change in the Polyribosome Fraction of Fra(X) Cells |
|---|---|---|---|---|
| KIAA 0964, PSD-95 assoc. SAPAP4 | absent | Hs. 177425 | Mm. 22094 | Decrease |
| UNC13 (*C. elegans*)-like protein (Munc 13) | 3' UTR | Hs. 155001 | Mm. 7872 | Decrease |
| KIAA 1091, Rab6 interacting protein 1 | coding region | Hs. 26797 | Mm. 21904 | Decrease |
| Similar to adenylate cyclase | unknown | Hs. 9572 | Mm. 41626 | Decrease |
| Similar to MKP-dusPTPase | absent | Hs. 29106 | Mm. 46262 | Decrease |
| TP63 | 3' UTR | Hs. 137569 | Mm. 54143 | Decrease |
| Casein kinase 1, gamma 2 | absent | Hs. 181390 | Mm. 29873 | Decrease |
| NAP-22 | coding region | Hs. 79516 | Mm. 29586 | Decrease |
| MAP1B | 5' UTR | Hs. 103042 | Mm. 36501 | Increase |
| Similar to I38022 hypothetical protein | unknown | Hs. 10299 | Mm. 24385 | Increase |
| KIAA0929 protein, Msx2 interacting nuclear target (MINT) homolog | coding region | Hs. 184245 | Mm. 25025 | Increase |
| KIAA0317 protein | 3' UTR | Hs. 20126 | Mm. 24446 | Increase |
| Arg/Ab1-interacting protein (ArgBP2) | absent | Hs. 278626 | Mm. 32247 | Increase |
| Transmembrane protein 1, TMEM1 (GT334) | 3' UTR | Hs. 94479 | Mm. 27539 | Increase |

A G-quartet structure has been described above as being identified in vitro as the RNA target of the RGG-box domain of FMRP. Of the 12 genes in Table 4 where sufficient sequence information existed for the analysis, eight (67%) genes showed the presence of a putative G-quartet structure. Considering that only 4% of a random collection of cDNAs are predicted as possible FMRP targets, the observation that 67% of the transcripts independently determined to both immunoprecipitate with FMRP and display a translational shift in the absence of FMRP certainly points to the G-quartet structure as being physiologically relevant in fragile X syndrome. A summary of several of the nucleic acid molecules and their corresponding UniGene and GenBank accession numbers is presented in Table 5 (below). Each of these sequences is available at, for instance, www.ncbi.nlm.nih.gov.

associated in vivo with the endogenous FMRP protein complex and to show translational changes in the absence of FMRP.

Example 17

Large-Scale Identification of FP-mRNP Associated mRNAs

The FMRP-immunoprecipitating mAb, 7G1-1, allows for the first time the purification of endogenous FMRP-mRNP complexes. The FMRP-mRNP complex was found to be associated with 3.9% of the expressed genes in mouse brain. The FMR1 message was not among these messages despite in vitro studies showing FMRP association with its own mRNA (Ashley et al. (1993) *Science* 262:563-566; Brown et al.

TABLE 5

Nucleic Acid Molecules Associated with the FMRP-mRNP and Corresponding GenBank Accession Numbers

| Nucleic Acid Molecule | Human UniGene; GenBank Accession Number | Mouse UniGene; GenBank Accession Number |
|---|---|---|
| KIAA 0964, PSD-95 assoc. SAPAP4 | Hs. 177425; AB023181 | Mm. 22094; BF019485 |
| UNC13 (*C. elegans*)-like protein (Munc 13) | Hs. 155001; NM_006377 | Mm. 7872; BB707186 |
| KIAA 1091, Rab6 interacting protein 1 | Hs. 26797; AB029014 | Mm. 21904; AJ245569 |
| EST, Similar to Adenylate Cyclase | Hs. 9572; R46369 | Mm. 41626; BF468002 |
| EST, Similar to MKP-dusPTPase | Hs. 29106; NM_020185 | Mm. 46262; AF237619 |
| TP63 | Hs. 137569; AF075430 | Mm. 54143; BB197042 |
| Casein kinase 1, gamma 2 | Hs. 181390; NM_001319 | Mm. 29873; BC004839 |
| NAP-22 | Hs. 79516; NM_006317 | Mm. 29586; AK011545 |
| MAP1B | Hs. 103042; NM_005909 | Mm. 36501; AI839626 |
| EST, Similar to I38022 hypothetical protein | Hs. 10299; AK023607 | Mm. 24385; BF134233 |
| KIAA0929 protein, Msx2 interacting nuclear target (MINT) homolog | Hs. 184245; AB023146 | Mm. 25025; AF156529 |
| KIAA0317 protein | Hs. 20126; NM_014821 | Mm. 24446; BC006074 |
| Arg/Ab1-interacting protein (ArgBP2) | Hs. 278626; NM_021069 | Mm. 32247; AK011482 |
| Transmembrane protein 1, TMEM1 (GT334) | Hs. 94479; U61500 | Mm. 27539; W29889 |
| Sec7-rel., KIAA0763 | Hs. 4764; AB018306 | Mm. 89798; BF164393 |
| Tyrosine Kin., AATYK | Hs. 128316; NM_004920 | Mm. 6826; NM_007377 |
| iGluR, kainate-R 5g2, Grik5 | Hs. 306463; AL137705 | Mm. 2879; NM_008168 |
| Brain Angiogen. Inh., BAI2 | Hs. 200586; NM_001703 | Mm. 4281; BI415619 |
| Zn.finger Mtsh-1 | Hs. 284217; BC010679 | Mm. 23862; AF191309 |
| Arf GTPase acivator, GIT1 | Hs. 318339; NM_014030 | Mm. 29593; AI841159 |
| Pumilio 2 | Hs. 6151; AF315591 | ; AF315590 |
| GAP-assoc. p190 | Hs. 102548; AF159851 | Mm. 28646; BI412535 |
| EST, Similar to KIAA0561 | ; AB01113 | Mm. 27047; AW553439 |

Table 5. Summary of certain nucleic acid molecules associated with the FMRP-mRNP and corresponding GenBank accession numbers.

Example 16

Identification of RNAs Associated In Vivo with FMRP

Soon after the discovery of the FMR1 gene, FMRP was recognized as an RNA-binding protein, although the in vivo target RNAs have remained elusive (Ashley et al. (1993) *Science* 262:563-566); 1993; Siomi et al., 1993). The work described here is the first to identify the repertoire of RNAs (1998) *J. Biol. Chem.* 273:15521-15527). The FMR1 message was detected at a moderate level in the wt brain lysate, with an input (baseline) average difference value of 114 and undetected, as expected, in KO input lysate. In comparison, 32% of the expressed genes had signal intensities higher than the FMR1 in the input lysate. There was a moderate 4.2 fold increase in the FMR1 transcript when the wt-IP RNA was compared to the KO-IP RNA (average difference change of 225), but no enrichment was found when comparing the wt-IP RNA to the wt input RNA. Although the FMR1 transcript may be a legitimate FMRP ligand, in light of the data presented here, it is likely there are other messages with much more avidity to this mRNP complex. Indeed, in contrast to FMR1, other mRNAs were detected at extremely low levels in the wt brain lysate input, yet were greatly enriched in the FMRP-mNP. This group includes messages predicting a KIAA0561-like protein, the Rab3 GDP/GTP exchange protein, and the Celera mRNA hCT25324 which is predicted by TBLASTX to encode an ubiquitin-ligase-like protein. In these cases, these messages were called as 'absent' in the input lysate. Yet, the average difference changes were 1114, 1270, and 916, respectively, in the IP vs. the input, indicating substantially greater relative abundance in the immunoprecipitated mRNP.

Quantitative RT-PCR using light-cycler technology confirmed that a tested subset of transcripts predicted to be enriched by the microarray data were indeed approximately 30- to 60-fold enriched in the wt-IP relative to the wt input lysate. This included the top ranking transcript in Table 2, the Sec7-related guanine nucleotide exchange factor, which was confirmed in independent lysates to be approximately 61-fold enriched in the FMRP-mRNP. It should be noted however, that given the 3' bias and the relatively short interval of cDNA sequence used in designing the oligonucleotide sequences of microarrays, false negatives occur, perhaps due to alternative splicing or to consolidation of gene family members. A case in point is the NAP-22 transcript. On the Mu19K microarray, NAP-22 was enriched in the wt-IP but subsequently failed to be scored highly on the MG-U74 microarray. After noting that NAP-22 displays a translational shift in the absence of FMRP, the association of the NAP-22 transcript with the FMRP-mRNP was re-investigated using quantitative RT-PCR and shown to be 63-fold enriched in the wt-IP relative to the total brain lysate. Since the newer MG-U74 microarray used EST-derived sequence to develop different oligonucleotides than those used in the Mu19K microarray, it is probable the two microarrays may be assaying different isoforms or family members for some genes. While it is likely the number of such genes is not high, this discrepancy, along with the relatively high stringency of analysis given herein, suggests this is an underestimation of the number of transcripts associated with the FMRP-mRNP.

Example 18

Altered Polyribosomal-Association of mRNAs in the Absence of FMRP

It has been hypothesized that FMRP may be incorporated into an mRNP-complex with its mRNA ligands and, in turn, associate with translating polyribosomes, somehow modulating the translation of those mRNA ligands (Jin and Warren (2000) *Hum. Mol. Genet.* 9:901-908). Using microarrays, a subset of mRNAs that are altered in the high-molecular-weight polyribosome fraction of fragile X cells have now been identified, most of which (251 out of 282) did not change in abundance in the total mRNA. These changes may imply an alteration in translation regulation in the absence of FMRP. Considering that synaptic abnormalities have been reported in both fragile X syndrome patients and the FMR1 knockout mouse, it is of substantial interest that several of the mRNAs that exhibited an abnormal polyribosome shift in fragile X syndrome cells are involved in neuronal plasticity and development/maturation of synapses, including NAP-22, neuritin, synaptosomal-associated protein 23, MAP B, UNC13-like protein, and SAPAP4 (Aravamudan et al. (1999) *Nat. Neurosci.* 2:965-971; Augustin et al. (2001) *J. Neurosci.* 21:10-7; Caroni (1997) *Bioessays* 19:767-775; Edelmann et al. (1996) *Proc. Natl. Acad. Sci. USA* 93:1270-1275; Frey et al. (2000) *J. Cell Biol.* 149:1443-1454; Hinton et al. (1991) *Am. J. Med. Genet.* 41:289-294; Naeve et al. (1997); Nimchinsky et al. (2001) *J. Neurosci.* 21:5139-5146; Takeuchi et al. (1997) *J. Biol. Chem.* 272:11943-11951).

Example 19

FMRP-Specific mRNA Ligands and a G-Quartet Structure

Comparing the genes identified in the complementary approaches, only 2% of the expressed genes surveyed showed a translational shift in the absence of FMRP, yet 50% of this subset of transcripts were also found in the FMRP-mRNP complex. These data strongly support the notion that the FMRP-mRNP complex recognizes specific mRNAs and modulates their translation on polyribosomes.

It has been hypothesized that RNA-binding proteins in mRNP complexes interact with specific cis elements in a subset of mRNAs, allowing the transcripts to be regulated at the posttranscriptional level (Keene (1999) *Proc. Natl. Acad. Sci. USA* 96:5-7; Tenenbaum et al. (2000) *Proc. Natl. Acad. Sci. USA* 97:14085-14090). This hypothesis predicts that one or more structural elements may be in common among a set of mRNAs found in mRNP complexes. Indeed, such a structural element, in the form of a G-quartet, has been identified in FMRP RNA ligands as described above. It is remarkable that 67% of the transcripts that both immunoprecipitate with the FMRP-mRNP complex in the mouse brain and display a translational shift in the patient cells are predicted to contain a G-quartet structure. Indeed, as described above, 11 messages in Table 4 bind to FMRP in vitro with affinities ranging from 194 nM to 599 nM. Moreover, the top ranked Sec7-related guanine nucleotide exchange factor (Table 2) is predicted to have a strong G-quartet structure, binds FMRP in vitro with an affinity of 322 nM, and shows $Li^+$ binding sensitivity, indicative of a G-quartet element. In addition, messages predicted to be FMRP ligands have been tested and two candidates examined (ID3 and V1a receptor) were both observed to be enriched in the FMRP immunoprecipitates from mouse brain. Of four candidates in humans, two, semaphorin 3F and, again, the V1a receptor were, decreased in the polyribosome fractions of patient cells (5.5- and 2-fold, respectively) but were unchanged in their total RNA abundance in cytoplasmic lysates.

Example 20

FMRP mRNA Ligands and the Pathogenesis of Fragile X Syndrome

The above results suggest roughly 4% of brain transcripts are possible targets for FMRP. Given the relatively subtle features of fragile X syndrome, it might be considered surprising that the translational alteration of such a substantial number of messages does not lead to a more severe phenotype. However, it may be only a smaller subset of mRNAs, perhaps those with the greatest binding affinity to FMRP, that are most influenced by the absence of FMRP. In addition the translational shifts seen in the absence of FMRP does not completely remove the affected transcripts from the polyribosomes. Accordingly, it would be expected that some of the encoded protein of the affected transcripts would still be produced. Thus the consequence of the absence of FMRP may indeed be a rather subtle cellular affect, perhaps most damaging in sensitive regions of localized protein synthesis, such as in neuronal processes.

The identified transcripts reported above encode a myriad of proteins involved in neuronal function. The top-ranked probe set is the mouse ortholog of the human transcript for the Sec7-related guanine-nucleotide exchange factor (Jackson and Casanova (2000) *Trends Cell Biol.* 10:60-67; Mayer et al. (2001) *Proc. Natl. Acad. Sci. USA* 98:4961-4965). Sec7 itself associates with Munc13, a phorbol ester receptor, and ARF, an ADP-ribosylation factor, and these proteins are together involved in Golgi vesicle maturation and vesicle transport in neurons (Augustin et al. (2001) *J. Neurosci.* 21:10-7; Neeb et al. (1999) *Eur. J. Cell Biol.* 78:533-538). Similarly, many of the other messages found (Table 2) associated with the FMRP-mRNP complex compose an interesting mix of novel messages and those whose encoded functions are intriguing in light of fragile X syndrome. For example, messages encoding proteins such as SAPAP4, DAP-1, and the kainate receptor Grik2 were enriched in the FMRP immunoprecipitation, and these proteins are found closely associated with the post-synaptic density and are involved in maintaining the PSD structure and neuronal cell signaling (El-Husseini et al. (2000) *Science* 290:1364-1368; Paschen et al. (1994) *Genomics* 20:435-440; Satoh et al. (1997) *Genes Cells* 2:415-424; Takeuchi et al. (1997) *J. Biol. Chem.* 272:11943-11951). Recent studies showing abnormal maturation and arborization of hippocampal neurons from FMR1 KO mice and fragile X patients are consistent with the altered translation of these and other post-synaptic proteins (Braun and Segal (2000) *Cereb. Cortex* 10:1045-1052; Hinton et al. (1991) *Am. J. Med. Genet.* 41:289-294; Nimchinsky et al. (2001) *J. Neurosci.* 21:5139-5146; Weiler et al. (1997) *Proc. Natl. Acad. Sci. USA* 94:5395-5400). Given the phenotypic overlap between fragile X syndrome and other neuropsychiatric disorders such as autism and attention deficit/hyperactivity, the mRNAs identified here may be considered a cache of candidate genes for these disorders as well.

Example 21

Experimental Procedures

Antibodies

Monoclonal antibody 7G1-1 was generated by immunizing FMR1 knock-out mice (The Dutch-Belgian Fragile X Consortium, 1994) with hexahistidine-tagged FMRP. The FMRP-epitope recognized by 7G1-1 was identified by screening an expression library prepared from a partial exonuclease/DNAse digestion of the FMR1 cDNA cloned into Novatope vector Novagen). Competitive Western blot and immuoprecipitation were done to confirm the epitope. Anti-FLAG M2 was from Sigma-Aldrich.

Mouse Brain Lysate Immunoprecipitation and Analysis

Whole brains from adult wt and FMR1 congenic C57B/6J littermates were harvested and homogenized in 2 ml/brain ice-cold buffer (10 mM Hepes, pH 7.4, 200 mM NaCl, 30 mM EDTA, 0.5% Triton X-100) with 2×complete protease inhibitors (Boehringer-Mannheim) and 400 U/ml rRNAsin (Promega) (Ishizuka et al. (1999) *Neuroscience* 88:295-306; Li et al. (1998) *J. Neurochem.* 71:2178-2185). All further manipulations of the brain lysates were performed at 4° C. After pelleting nuclei, the supernatants were raised to 400 mM NaCl, and clarified. The resulting supernatant was precleared and an aliquot (20%) of precleared supernatant ('input') was saved for RNA extraction. The remaining lysate was immunoprecipitated with 7G1-1 mAb. The immunoprecipitate was resuspended in DEPC-H$_2$0 for protein analysis and RNA extraction Linear Sucrose Gradient Fractionation Linear sucrose gradient fractionation was performed as described (Eisen et al. (1998) *Proc. Natl. Acad. Sci. USA* 95:14863-14868; Feng et al. (1997) *Mol. Cell* 1:109-118). EBV-transformed human lymphoblastoid cell lines, including normal cells (J1, AP107, CM15A, EuH154 and TN7) and fragile X cells (GM3200A, NB118, GM07294, OS9 and KJH172), were cultured at 37° C. with the density of $5\times10^5 \sim 1\times10^6$/ml. After incubating with cycloheximide (100 µg/ml) to arrest polyribosome migration, five different cell lines (normal or fragile X) were pooled. Cell cytoplasmic lysates were fractionated by bottom displacement using a gradient fractionator (ISCO) with the ribosomal profile monitored at OD$_{254}$.

RNA Isolation and Oligonucleotide Array Expression Analysis

In immunoprecipitation experiments, RNA from precleared 'Input' lysate was isolated using Trizol reagent (Gibco BRL) and the RNeasy Mini Kit (QIAGEN). Immunoprecipitated RNA from the brains of both wt and FMR1 KO mice was phenol/chloroform extracted and ethanol precipitated. To isolate the RNA from polyribosomes, phenol/chloroform extraction and ethanol precipitation were performed and RNA isolated using the RNeasy Mini Kit (QIAGEN). In addition, total RNA from whole cells treated with cycloheximide was isolated using RNeasy Mini Kit (QIAGEN).

The cRNA 'targets' were generated following manufactural instructions (www.affymetrix.com). In immunoprecipitation experiments, one fifth of the precleared 'Input' lysate was used to generate Input cRNA. Sixty percent of the wt-IP and the KO-IP RNA was used to generate IP-cRNA targets and was sequentially hybridized to Murine Genome U74 array (subsets A, B, and C) or to Murine 19K array (subsets A, B, and C). Absolute and Comparison analyses were performed using Affymetrix Microarray Suite 4.0 software. A recently released mask files to exclude uninformative antisense probe sets from the MG-U74 analyses were applied (www.affymetrix.com). The wt-IP RNA was compared to the KO-IP RNA baseline (scale factor 1, normalization 1). The data was filtered for probe sets 'present' and 'increased' in wt-IP RNA with a +4.0 fold change or greater. This data was further filtered by comparing wt-IP RNA to the input RNA baseline (scale factor 150, normalization 1), selecting for probe sets 'present' and 'increased' in wt-IP RNA with a +4.0 fold change or greater. Mu19K data comparisons of wt-IP versus the input RNA were performed using the same parameters. In polyribosomal mRNA profile analysis, cRNAs generated from polyribosomal fractions and total mRNA were hybridized to Human 35K (Hu35K) arrays. All the arrays were scaled to an average intensity of 500 and analyzed independently using Affyinetrix Microarray Suite 4.0 software. The dendrogram was generated using GENECLUSTER, as described (Eisen et al. (1998) *Proc. Natl. Acad. Sci. USA* 95:14863-14868).

cDNA Synthesis, RT-PCR and LightCycler Real-Time PCR

The first strand cDNA was generated by reverse transcription with oligo dT primer or random hexamers. The $^{32}$P-UTP-labeled first strand cDNA was analyzed via surface-tension agarose gel electrophoresis. In RT-PCR analysis, one microliter of the RT reaction was used in a 27-cycle PCR reaction for each target gene, and products were analyzed by agarose gel electrophoresis. To quantify the mRNA levels, using the LightCycler (Roche Molecular Biochemicals), aliquots of first stranded cDNA were amplified and real-time fluorimetric intensity of SYBR green I was monitored. The ratio of different samples was calculated by LightCycler Data Analysis Software (Roche Molecular Biochemicals).

RNA Slot Blotting

A half microgram of total RNA from normal or fragile X whole cell lysates and the same proportion of RNA from each fraction were used for RNA blotting using gene-specific cDNA probes.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

What is claimed is:

1. A method of determining a fragile X mental retardation protein (FMRP) target comprising the steps of:
   (a) searching a nucleic acid sequence database for nucleic acid sequences containing an FMRP target sequence;
   (b) identifying a nucleic acid sequence that contains said FMRP target sequence; and
   (c) assaying whether said nucleic acid binds to FMRP,
   wherein said FMRP target comprises a DWGG-N(0-2) DWGG-N(0-1)DWGG-N(0-1)DWGG consensus sequence set forth in SEQ ID NO:7.

2. The method of claim 1, wherein said searching and identifying steps are carried out using software capable of searching both structural and sequence-specific elements.

3. The method of claim 1, wherein the step of identifying a nucleic acid sequence that contains said FMRP target sequence further comprises predicting the fold of said sequence by use of software and discarding those sequences that have competing internal stems.

4. A method of isolating a nucleic acid molecule capable of binding fragile X mental retardation protein (FMRP), comprising:
   a) contacting said FMRP with a composition of nucleic acid molecules; and
   b) isolating a nucleic acid molecule binding said FMRP protein by immunoprecipitating said FMRP with an anti-FMRP monoclonal antibody,
      wherein said monoclonal antibody is the mouse monoclonal antibody 7G1-1 deposited with ATCC as PTA-3857.

5. The method of claim 4, further comprising the step of identifying said nucleic acid molecule.

6. The method of claim 5, wherein said identifying said nucleic acid molecule is carried out using a gene chip.

* * * * *